United States Patent
Verkman et al.

(10) Patent No.: US 6,201,116 B1
(45) Date of Patent: Mar. 13, 2001

(54) HALIDE INDICATORS

(75) Inventors: Alan S. Verkman; Joachim Biwersi; Sujatha Jayaraman, all of San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/277,354

(22) Filed: Mar. 26, 1999

(51) Int. Cl.[7] .................. C07H 5/06; C07D 239/00; C07D 471/00; C07D 487/00; G01N 21/76

(52) U.S. Cl. .................. 536/29.1; 544/251; 544/252; 436/172

(58) Field of Search .................. 514/25, 33, 35, 514/43; 536/4.1, 18.7, 29.1; 436/172; 544/251, 252

(56) References Cited

PUBLICATIONS

Skalski et al. "Fluorescent Nucleoside With A New Heterocyclic Betaine As The Aglycone Photochemical Preparation and Properties", Tetrahedron, vol. 43, No. 17, pp. 3955–3961, 1987.*

Verkman, A.S. "Development and biological applications of chloride–sensitive fluorescent indicators", Am. J. Physio., vol. 259, pp. C375–C388, 1990.*

Mielewcyzk et al. "Deoxyluminarosine: New Photochemically Prepared Fluorophore For The Sequence–Specific Oligonucleotide Labelling", Nucleosides and Nucleotides, vol. 10(1–3), pp. 263–267, 1991.*

Burdzy et al. "Photosensitized Preparation Of Fluorescent Luminarosine and Analogues", Nucleosides and Nucleotides, vol. 17(1–3), pp. 143–151, 1998.*

* cited by examiner

Primary Examiner—Howard C. Lee
(74) Attorney, Agent, or Firm—Richard Aron Osman

(57) ABSTRACT

The invention provides methods and compositions for measuring ion concentration inside a cell by measuring fluorescence of a compound of the general formula I. In particular embodiments, the measured ion is halide, particularly iodide, the cell contains a functional anion transport protein or channel, the method measures a change in fluorescence as a function of a predetermined condition such as the presence of a predetermined amount of a candidate modulator of ion transport in the cell (e.g. for drug screening) or the expression by the cell of a transgene (e.g. to assess the efficacy of gene therapy).

30 Claims, No Drawings

HALIDE INDICATORS

INTRODUCTION TO THE INVENTION

1. Field of the Invention

The field of the invention is halide indicators and their use in detecting anion transport.

2. Background

Several halide-sensitive fluorescent indicators have been introduced to study the functional properties of Cl⁻ transporters in biomembrane vesicles and living cells and epithelial tissues (for review, see Verkman, 1990; Verkman and Biwersi, 1995). The archetype indicator SPQ (6-methoxy-N-[3-sulfopropyl]quinolinium, Illsley and Verkman, 1987) is a polar quinolinium compound whose fluorescence is quenched by Cl⁻ and I⁻ by a collisional mechanism. SPQ and related quinolinium indicators have been useful in studying the CFTR (Cystic Fibrosis Transmembrane conductance Regulator) Cl⁻ channel expressed in native and transfected cell models (e.g. Brown et al., 1996), and recently, in assaying functional CFTR delivery in human gene therapy trials (McLachlan et al., 1996; Porteous et al., 1997; Gill et al., 1997). Various SPQ derivatives have been synthesized for specific applications including cell-permeable/trappable compounds (Biwersi and Verkman, 1991), dual-wavelength Cl⁻ indicators for ratio imaging (Jayaraman et al., 1999), dextran-linked conjugates (Biwersi et al., 1992), and fiberoptic halide sensors (Kao et al., 1992).

Although used in numerous studies of CFTR function in cell culture models, the existing quinolinium-based halide indicators have imperfect optical and physical properties that limit their utility in more challenging applications including the analysis of CFTR function in gene therapy trials and high-throughput drug screening. SPQ and related indicators have relatively dim fluorescence in cells (molar extinction <6000 $M^{-1}$ $cm^{-1}$, quantum yield <0.1) and require ultraviolet excitation (excitation 320–365 nm, emission 420–460 nm). Significant technical limitations include the need for sensitive detection instrumentation with high numerical aperture optics, and the background autofluorescence resulting from ultraviolet excitation. In addition, the quinolinium halide indicators are quenched by intracellular proteins and organic anions, resulting in decreased cytoplasmic Cl⁻ sensitivity and dependence of indicator fluorescence on changes in cell volume (Chao et al., 1989; Srinivas and Bonanno, 1997). We previously synthesized long-wavelength Cl⁻ indicators containing the acridinium chromophore (Biwersi et al., 1994); although these indicators have been useful to study Cl⁻ transport in liposomes and biomembrane vesicles, they are chemically unstable in cytoplasm—a problem that could not be overcome by derivatization.

The present invention provides bright, long-wavelength halide indicators and their uses in assays of CFTR-mediated anion conductance in living cells, particularly a sensitive, robust anion transport assay suitable for high-throughput drug screening. The specifications of the indicator(s) include: high Cl⁻ and/or I⁻ sensitivity, bright fluorescence with excitation wavelength >400 nm and emission wavelength >500 nm, minimal photobleaching, lack of cellular toxicity, rapid loading into cytoplasm, uniform distribution and chemical stability in cytoplasm, and low leakage out of cells.

SUMMARY OF THE INVENTION

The invention provides methods and compositions for measuring ion concentration inside a cell by measuring fluorescence of a compound of the general formula I:

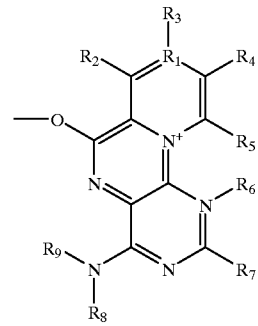

wherein $R_1$ is selected from C and N, and $R_2$–$R_9$ are independently selected from the group consisting of substituted or unsubstituted alkylalkenyl, alkynyl, aryl, heteroalkyl, heteroaryl, and acyl substituents, wherein one or more of the pairs $R_2$ and $R_3$, $R_3$ and $R_4$, $R_4$ and $R_5$, $R_6$ and $R_7$, and $R_8$ and $R_9$, may be directly or indirectly further covalently connected, to form a substituted or unsubstituted, aromatic or nonaromatic ring. The methods encompass the use of wide variety of particular embodiments, derivatives, analogs, etc. of the generic compound. In particular embodiments, the measured ion is halide, particularly iodide, the cell contains a functional anion transport protein or channel, the method measures a change in fluorescence as a function of a predetermined condition such as the presence of a predetermined amount of a candidate modulator of ion transport in the cell (e.g. for drug screening) or the expression by the cell of a transgene (e.g. to assess the efficacy of gene therapy).

The subject compositions comprise a compound comprising the general formula I, wherein (a) one or more of the pairs $R_2$ and $R_3$, $R_3$ and $R_4$, $R_4$ and $R_5$, $R_6$ and $R_7$, and $R_8$ and $R_9$, is further covalently connected, to form a substituted or unsubstituted, aromatic or nonaromatic ring, (b) one or more of $R_2$–$R_7$ comprises a functional group, and/or (c) $R_1$ is N. In particular embodiments, the functional group is a conjugation group, a polarity enhancing group or an iodide sensitivity enhancing group, and in a more particular embodiment, the conjugation group is coupled to a moiety selected from a membrane impermeable molecule, an optical sensor and a chromophore. A wide variety of additional particular embodiments of the generic compound as well as numerous exemplary compounds are disclosed. For example, preferred compounds provide one or more of: threshold molar extinctions, quantum yields, excitation wavelengths and emission wavelengths, fluorescence, relatively specific iodide quenching, relatively low cytotoxicity, relatively low photobleaching in cells, relatively uniform distribution in cells, relatively high chemical stability in cells, relatively low leakage out of cells and relatively rapid loading into cells.

DESCRIPTION OF PARTICULAR EMBODIMENTS OF INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

The general invention methods involve measuring ion concentration inside a cell by detecting fluorescence inside the vesicle of a compound of the general formula I. Pursuant to the general formula, $R_2$–$R_9$ are independently selected from the group consisting of substituted or unsubstituted alkyl, alkenyl, alkynyl, aryl, heteroalkyl, heteroaryl, and acyl substituents.

Exemplary such substituents may be independently selected from:

hydrogen,
    substituted or unsubstituted (C1–C10)alkyl,
    substituted or unsubstituted (C1–C10)alkoxy,
    substituted or unsubstituted (C3–C6)alkenyl,
    substituted or unsubstituted (C2–C6)heteroalkyl,
    substituted or unsubstituted (C3–C6)heteroalkenyl,
    substituted or unsubstituted (C3–C6)alkynyl,
    substituted or unsubstituted (C3–C8)cycloalkyl,
    substituted or unsubstituted (C5–C7)cycloalkenyl,
    substituted or unsubstituted (C5–C7)cycloalkadienyl,
    substituted or unsubstituted aryl,
    substituted or unsubstitated aryloxy,
    substituted or unsubstituted aryl-(C3–C8)cycloalkyl,
    substituted or unsubstituted aryl-(C5–C7)cycloalkenyl,
    substituted or unsubstituted aryloxy-(C3–C8)cycloalkyl,
    substituted or unsubstituted aryl-(C1–C4)alkyl,
    substituted or unsubstituted aryl-(C1–C4)alkoxy,
    substituted or unsubstituted aryl-(C1–C4)heteroalkyl,
    substituted or unsubstituted aryl-(C3–C6)alkenyl,
    substituted or unsubstituted aryloxy-(C1–C4)alkyl,
    substituted or unsubstituted aryloxy-(C2–C4)heteroalkyl,
    substituted or unsubstituted heteroaryl,
    substituted or unsubstituted heteroaryloxy,
    substituted or unsubstituted heteroaryl-(C1–C4)alkyl,
    substituted or unsubstituted heteroaryl-(C1–C4)alkoxy,
    substituted or unsubstituted heteroaryl-(C1–C4)heteroalkyl,
    substituted or unsubstituted heteroaryl-(C3–C6)alkenyl,
    substituted or unsubstituted heteroaryloxy-(C1–C4)alkyl, and
    substituted or unsubstituted heteroaryloxy-(C2–C4)heteroalkyl.

Substituents for the alkyl, alkoxy, alkenyl, heteroalkyl, heteroalkenyl, alkynyl, cycloalkyl, heterocycloalkyl, cycloalkenyl, and cycloalkadienyl radicals may be selected independently from —H
—OH
—O—(C1–C10)alkyl
=O—$NH_2$
—NH—(C1–C10)alkyl
—N[(C1–C10)alkyl]$_2$
—SH
—S—(C1–C10)alkyl
—halo
—Si[(C1–C10)alkyl]$_3$ in a number ranging from zero to (2N+1), where N is the total number of carbon atoms in such radical.

Substituents for the aryl and heteroaryl groups may be selected independently from
—halo
—OH
—O—R'
—O—C(O)—R'
—$NH_2$
—NHR'
—NR'R"
—SH
—SR'
—R'
—CN
—$NO_2$
—$CO_2$H
—$CO_2$—R'
—$CONH_2$
—CONH—R'
—CONR'R"
—O—C(O)—NH—R'
—O—C(O)—NR'R"
—NH—C(O)—R'
—NR"—C(O)—R'
—NH—C(O)—OR'
—NR"—C(O)—R'
—NH—C($NH_2$)=NH
—NR'—C($NH_2$)=NH
—NH—C($NH_2$)=NR'
—S(O)—R'
—S(O)$_2$—R'
—S(O)$_2$—NH—R'
—S(O)$_2$—NR'R"
—$N_3$
—CH(Ph)$_2$ substituted or unsubstituted aryloxy
substituted or unsubstituted arylamino
substituted or unsubstituted heteroarylamino
substituted or unsubstituted heteroaryloxy
substituted or unsubstituted aryl-(C1–C4)alkoxy,
substituted or unsubstituted heteroaryl-(C1–C4)alkoxy,
perfluoro(C1–C4)alkoxy, and
perfluoro(C1–C4)alkyl,
in a number ranging from zero to the total number of open valences on the aromatic ring system;
and where R' and R" are independently selected from:
    substituted or unsubstituted (C1–C10)alkyl,
    substituted or unsubstituted (C1–C10)heteroalkyl,
    substituted or unsubstituted (C2–C6)alkenyl,
    substituted or unsubstituted (C2–C6)heteroalkenyl,
    substituted or unsubstituted (C2–C6)alkynyl,
    substituted or unsubstituted (C3–C8)cycloalkyl,
    substituted or unsubstituted (C3–C8)heterocycloalkyl,
    substituted or unsubstituted (C5–C6)cycloalkenyl,
    substituted or unsubstituted (C5–C6)cycloalkadienyl,
    substituted or unsubstituted aryl,
    substituted or unsubstituted aryl-(C1–C4)alkyl,
    substituted or unsubstituted aryl-(C1–C4)heteroalkyl, substituted or unsubstituted aryl-(C2–C6)alkenyl,
substituted or unsubstituted aryloxy-(C1–C4)alkyl,
substituted or unsubstituted aryloxy-(C1–C4) heteroalkyl,
substituted or unsubstituted heteroaryl,
substituted or unsubstituted heteroaryl-(C1–C4)alkyl,
substituted or unsubstituted heteroaryl-(C1–C4) heteroalkyl,
substituted or unsubstituted heteroaryl-(C2–C6) alkenyl,
substituted or unsubstituted heteroaryloxy-(C1–C4) alkyl, and
substituted or unsubstituted heteroaryloxy-(C1–C4) heteroalkyl.

In a particular embodiment, one or more of $R_2$–$R_7$, preferably one or more of $R_2$–$R_5$, comprises a functional group. In a particular embodiment, the functional group is a conjugation group selected from $R_{10}NR_{11}R_{12}$, $R_{10}COOR_{13}$, or $R_{10}X$, wherein X is halide, $R_{10}$ is alkyl and $R_{11}$–$R_{13}$ are independently selected from the group consisting of substituted or unsubstituted alkyl, alkenyl, alkynyl, aryl, heteroalkyl, heteroaryl, and acyl substituents. In a more particular embodiment, $R_{10}$ is $(CH_2)_n$, wherein n is an integer from 0–3. In another more particular embodiment, the conjugation group is coupled to a moiety selected from a membrane impermeable molecule, such as dextran, ficol, PEG (polyethyleneglycol) or other macromolecule, including biomolecules such as proteins, polysaccharides, etc.; an optical sensor, such as activated glass beads or fibers, see, e.g. Kao et al. (1992) Proc SPIE 1648, 194–201, and a chromophore, such as rhodamine, BODIPY (Molecular Probes, Eugene Oreg.), TEXAS RED (Molecular Probes, Eugene Oreg.), etc., especially chromophores that provide a second, different color from the core chromophore, and hence a dual wavelength indicator (see Examples for applications).

In another particular embodiment, the functional group is a polarity enhancing group selected from $R_{10}SO_3^-$, $R_{10}COO^-$, $R_{10}NR_{11}R_{12}R_{13}^+$, wherein $R_{10}$ is alkyl and $R_{11}$–$R_{13}$ are independently selected from the group consisting of substituted or unsubstituted alkyl, alkenyl, alkynyl, aryl, heteroalkyl, heteroaryl, and acyl substituents. In a more particular embodiment, $R_{10}$ is $(CH_2)_n$, wherein n is an integer from 0–3.

In yet another particular embodiment, the functional group is an iodide sensitivity enhancing group selected from $R_{10}NR_{11}R_{12}$, $R_{10}CH_3$, $R_{10}OCH_3$, or $R_{10}COOR_{13}$, wherein $R_{10}$ is alkyl or a bond and $R_{11}$–$R_{13}$ are independently selected from the group consisting of substituted or unsubstituted alkyl, alkenyl, alkynyl, aryl, heteroalkyl, heteroaryl, and acyl substituents. In a more particular embodiment, $R_{10}$ is $(CH_2)_n$, wherein n is an integer from 0–3.

In other embodiments:

one or more of the pairs $R_2$ and $R_3$, $R_3$ and $R_4$, $R_4$ and $R_5$, $R_6$ and $R_7$, and $R_8$ and $R_9$, is further covalently connected, to form a substituted or unsubstituted, aromatic or nonaromatic ring structure. For example, where $R_4$ and $R_5$ are ethylene, the pair may be joined to form an aryl ring;

$R_1$ is N;

$R_1$ is C; $R_2$, $R_3$, $R_5$, $R_6$, $R_7$ and $R_9$ are H; $R_8$ is a polyhydroxylated cycloalkyl or cycloheteroalkyl; and $R_4$ comprises a functional group;

$R_1$ is C; $R_3$, $R_5$, $R_7$ and $R_9$ are H; $R_8$ is a polyhydroxylated cycloalkyl or cycloheteroalkyl; one of $R_2$, $R_4$ and $R_6$ comprises a functional group and the remaining two of $R_2$, $R_4$ and $R_6$ are H, wherein the functional group is a conjugation group selected from $R_{10}NR_{11}R_{12}$, $R_{10}COOR_{13}$, or $R_{10}X$, wherein X is halide, $R_{10}$ is alkyl and $R_{11}$–$R_{13}$ are independently selected from the group consisting of substituted or unsubstituted alkyl, alkenyl, alkynyl, aryl, heteroalkyl, heteroaryl, and acyl substituents;

$R_1$ is C; $R_3$, $R_5$, $R_7$ and $R_9$ are H; $R_8$ is a polyhydroxylated cycloalkyl or cycloheteroalkyl; one of $R_2$, $R_4$ and $R_6$ comprises a functional group and the remaining two of $R_2$, $R_4$ and $R_6$ are H, wherein the functional group is a polarity enhancing group selected from $R_{10}SO_3^-$, $R_{10}COO^-$, $R_{10}NR_{11}R_{12}R_{13}^+$, wherein $R_{10}$ is alkyl and $R_{11}$–$R_{13}$ are independently selected from the group consisting of substituted or unsubstituted alkyl, alkenyl, alkynyl, aryl, heteroalkyl, heteroaryl, and acyl substituents;

$R_1$ is C; $R_3$, $R_5$, $R_7$ and $R_9$ are H; $R_8$ is a polyhydroxylated cycloalkyl or cycloheteroalkyl; one of $R_2$, $R_4$ and $R_6$ comprises a functional group and the remaining two of $R_2$, $R_4$ and $R_6$ are H, wherein the functional group is an iodide sensitivity enhancing group selected from $R_{10}NR_{11}R_{12}$, $R_{10}CH_3$, $R_{10}OCH_3$, or $R_{10}COOR_{13}$, wherein $R_{10}$ is alkyl or a bond and $R_{11}$–$R_{13}$ are independently selected from the group consisting of substituted or unsubstituted alkyl, alkenyl, alkynyl, aryl, heteroalkyl, heteroaryl, and acyl substituents;

$R_1$ is C; $R_2$, $R_3$, $R_6$, $R_7$ and $R_9$ are H; $R_8$ is a polyhydroxylated cycloalkyl or cycloheteroalkyl, and the pair $R_4$ and $R_5$, is further covalently connected, to form a substituted or unsubstituted, aromatic ring structure; or $R_1$ is N; $R_2$–$R_7$ and $R_9$ are H; $R_8$ is a polyhydroxylated cycloalkyl or cycloheteroalkyl.

In yet more particular embodiments:

(a) $R_2$ and $R_3$ are ethylenes, joined to form an aryl ring; $R_1$ is C; $R_5$, $R_6$, $R_7$ and $R_9$ are H; $R_8$ is ribofuranosyl; and $R_4$ is propanyl.

(b) $R_4$ and $R_5$ are ethylenes, joined to form an aryl ring; $R_1$ is N; $R_2$, $R_3$, $R_6$, $R_7$ and $R_9$ are H; and $R_8$ is ribofuranosyl.

(c) $R_4$ and $R_5$ are ethylenes, joined to form an aryl ring; $R_1$ is C; $R_2$, $R_3$, $R_6$, and $R_9$ are H; $R_8$ is ribofuranosyl; and $R_7$ is methylamine.

(d) $R_6$ and $R_7$ are ethylenes, joined to form an aryl ring; $R_1$ is N; $R_2$, $R_3$, $R_5$ and $R_6$ are H; $R_8$ and $R_9$ are methoxy; and $R_4$ is butanyl.

(e) $R_1$ is C; $R_2$, $R_3$, $R_5$, $R_6$, $R_7$, $R_9$ and $R_{13}$ are H; $R_8$ is ribofuranosyl; $R_4$ is $R_{10}COOR_{13}$, wherein $R_{10}$ is methyl.

(f) $R_1$ is C; $R_2$, $R_3$, $R_5$, $R_6$, $R_7$, $R_9$, $R_{11}$ and $R_{12}$ are H; $R_8$ is ribofuranosyl; $R_4$ is $R_{10}NR_{11}R_{12}$, wherein $R_{10}$ is methyl.

(g) $R_1$ is C; $R_2$, $R_3$, $R_4$, $R_5$, $R_7$, and $R_9$ are H; $R_8$ is ribofuranosyl; $R_6$ is $R_{10}Cl$, wherein $R_{10}$ is ethyl.

(h) $R_1$ is C; $R_3$, $R_4$, $R_5$, $R_6$, $R_7$ and $R_9$, are H; $R_8$ is ribofuranosyl; $R_2$ is $R_{10}COOR_{13}$ wherein $R_{10}$ and $R_{13}$ are methyl.

(i) $R_1$ is C; $R_2$, $R_3$, $R_5$, $R_6$, $R_7$ and $R_9$ are H; $R_8$ is ribofuranosyl; $R_4$ is $R_{10}SO_3^-$, wherein $R_{10}$ is methyl.

(j) $R_1$ is C; $R_2$, $R_3$, $R_5$, $R_6$, $R_7$ and $R_9$ are H; $R_8$ is ribofuranosyl; $R_4$ is $R_{10}COO^-$, wherein $R_{10}$ is methyl.
(k) $R_1$ is C; $R_2$, $R_3$, $R_4$, $R_5$, $R_7$, and $R_9$ are H; $R_8$ is ribofuranosyl; $R_6$ is $R_{10}Cl$, wherein $R_{10}$ is ethyl.
(l) $R_1$ is C; $R_3$, $R_5$, $R_6$, $R_7$ and $R_9$, are H; $R_8$ is ribofuranosyl; $R_2$ is $R_{10}SO_3^-$, $R_4$ is $R_{11}SO_3$ wherein $R_{10}$ and $R_{11}$ are methyl.
(m) $R_1$ is C; $R_2$, $R_3$, $R_5$, $R_6$, $R_7$ and $R_9$ are H; $R_8$ is ribofuranosyl; $R_4$ is $R_{10}COOR_{13}$, wherein $R_{10}$ is a single bond and $R_{13}$ is methyl.
(n) $R_1$ is C; $R_2$, $R_3$, $R_5$, $R_7$ and $R_9$, are H; $R_8$ is ribofuranosyl; $R_4$ is $R_{10}NR_{11}R_{12}$, wherein $R_6$, $R_{10}$, $R_{11}$ and $R_{12}$ are methyl.
(o) $R_1$ is C; $R_2$, $R_3$, $R_4$, $R_5$, $R_7$, and $R_9$ are H; $R_8$ is glycerol; $R_6$ is $R_{10}CH_3$, wherein $R_{10}$ is propyl.
(p) $R_1$ is C; $R_3$, $R_4$, $R_5$, $R_6$, $R_7$ and $R_9$, are H; $R_8$ is ribofuranosyl; $R_2$ is $R_{10}COOR_{13}$ wherein $R_{10}$ is a single bond and $R_{13}$ is methyl.
(q) $R_1$ is C; $R_3$, $R_4$, $R_5$, $R_6$, $R_7$ and $R_9$, are H; $R_8$ is ribofuranosyl; $R_2$ is $R_{10}OCH_3$ wherein $R_{10}$ is a single bond and $R_{13}$ is ethyl.

Further exemplary compounds and exemplary synthetic schemes include:

1. 7-(β-D-ribofuranosylamino)-2-(n-carboxyalkyl) pyrido [2,1-h]pteridin-11-ium-5-olate, n=1–3; Synthesis:

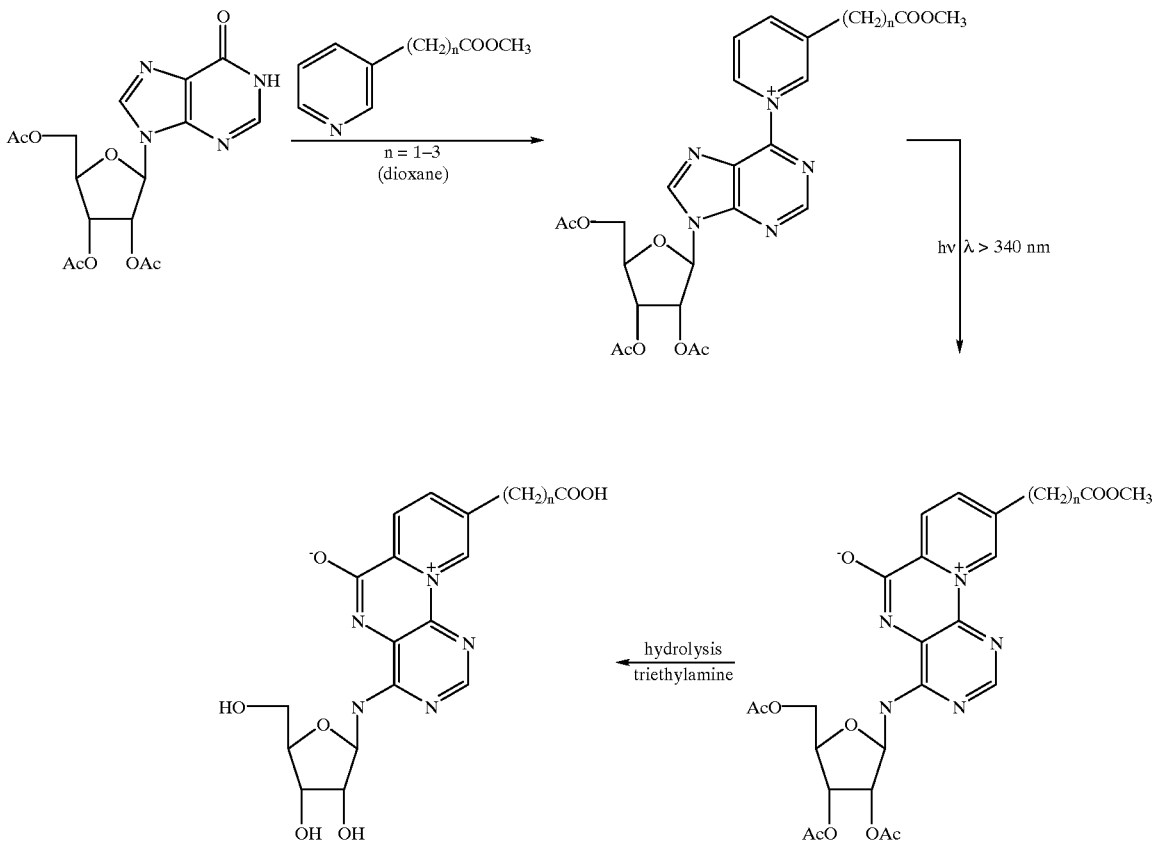

2. 7-(β-D-ribofuranosylamino)-2-(n-aminoalkyl) pyrido [2,1-h]pteridin-11-ium-5-olate, n=1–3; Synthesis:

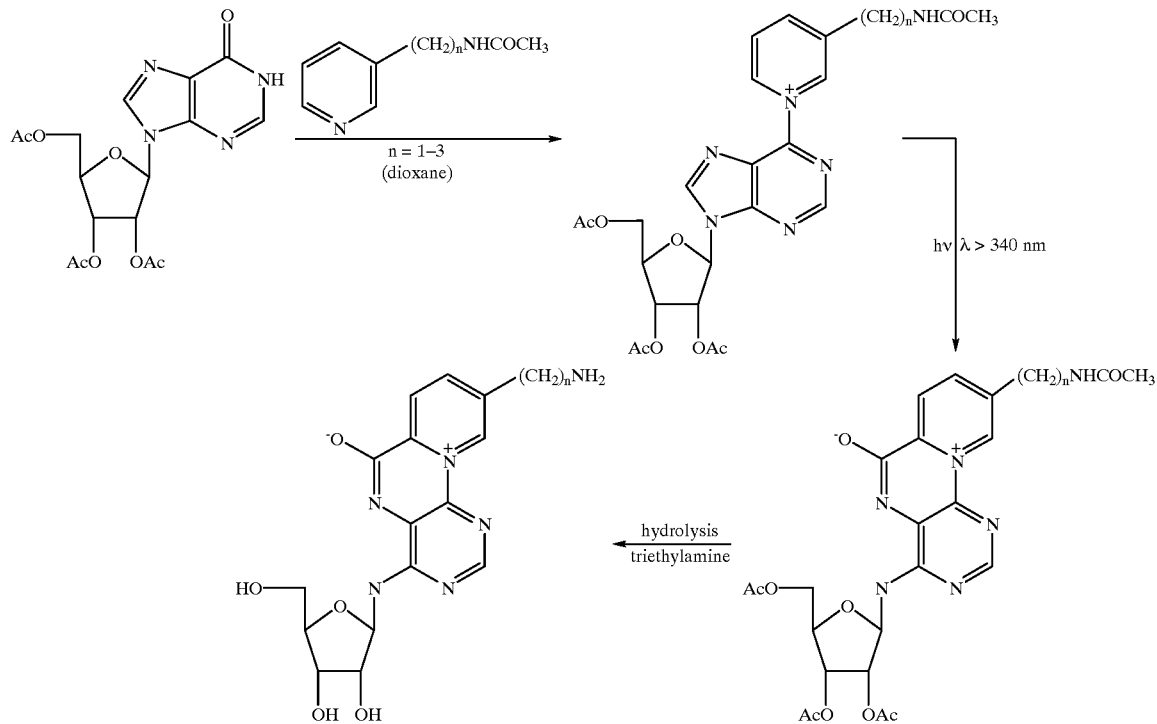
3. 7-(β-D-ribofuranosylamino)-2-(n-chloroalkyl) pyrido
   [2,1-h]pteridin-11-ium-5-olate, n=1–3; Synthesis:
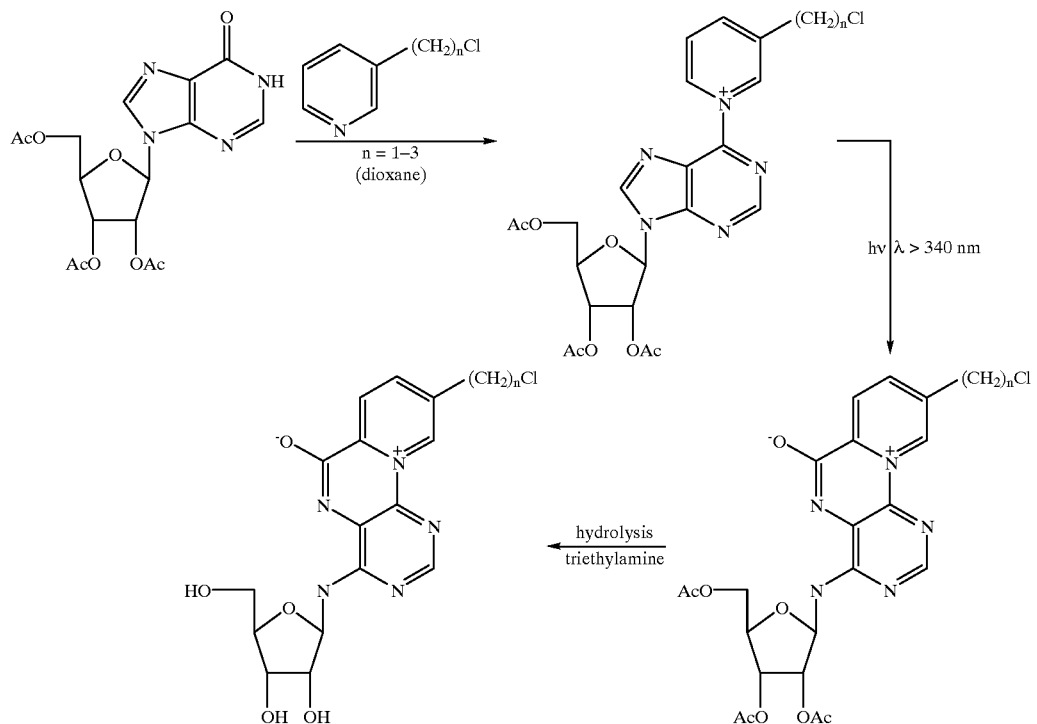
4. 7-(β-D-ribofuranosylamino)-2-carboxy pyrido[2,1-h]
   pteridin-11-ium-5-olate; Synthesis:

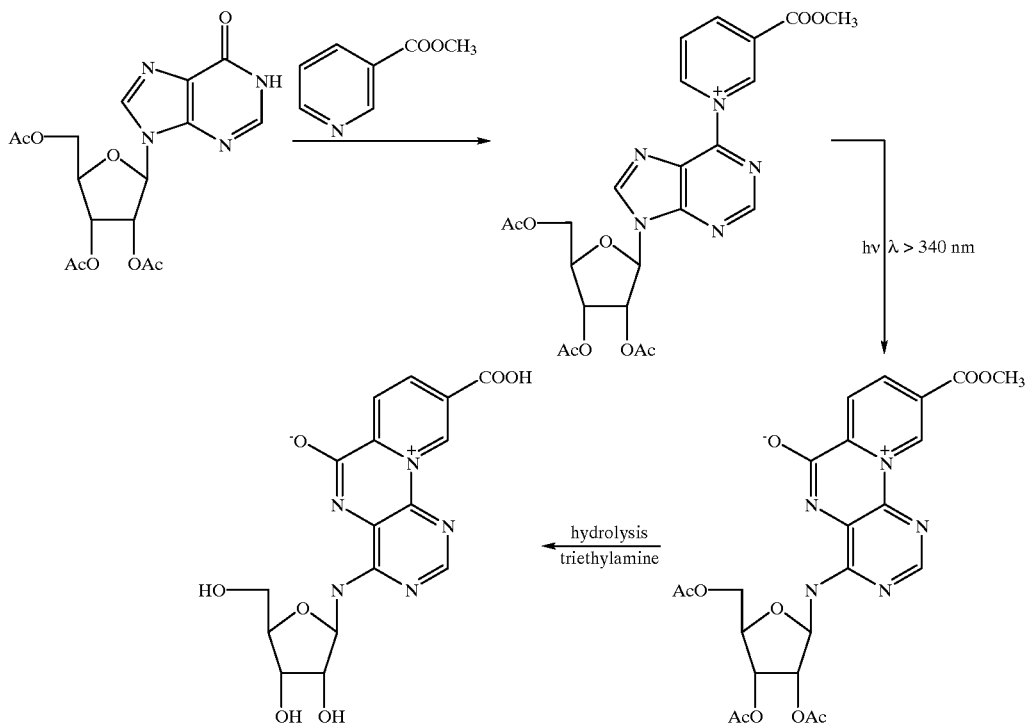

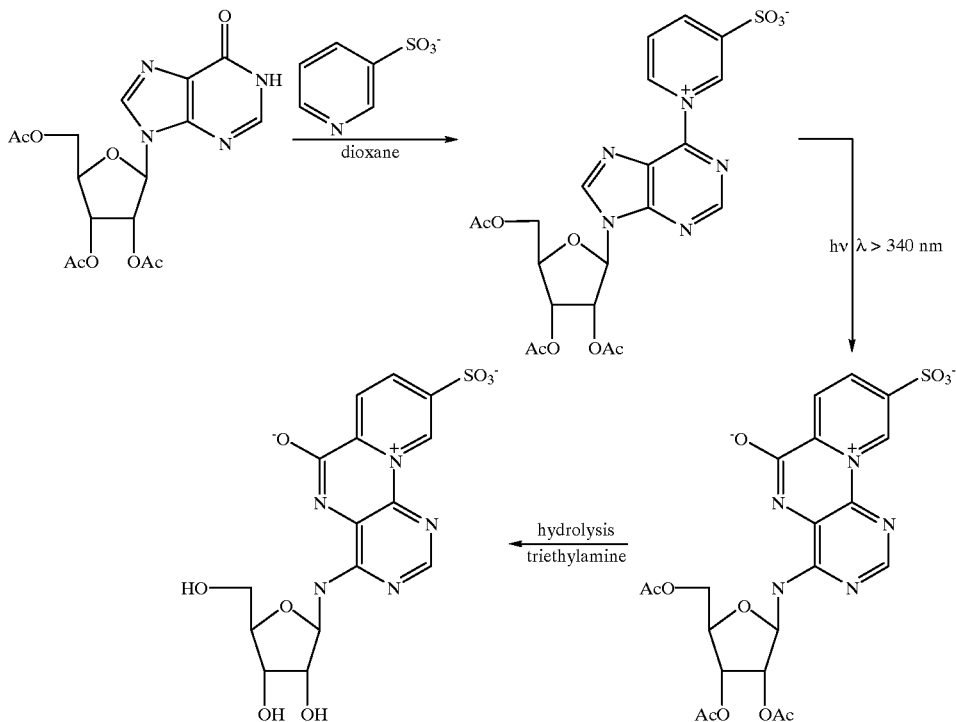

5. 7-(β-D-ribofuranosylamino)-2-sulfonato pyrido[2,1-h]pteridin-11-ium-5-olate; Synthesis:

The compounds used in the methods, including those specifically disclosed supra, provide detectable fluorescence and demonstrate one or more of:

(1) relatively specific ion, preferably halide, more preferably iodide quenching, wherein specificity provides a Stern-Volmer constant difference of at least 5, preferably at least 10, more preferably at least 20, most preferably at least 50-fold in specific vs. non-specific constants; preferred compounds also provide fluorescence to intracellular I⁻ of strength sufficient to permit measurements of Cl⁻/I⁻ exchange using less than 50, preferably less than 10, more preferably less than 5, most preferably less than 2 mM I⁻ according to experiments as shown in Example 1;

(2) relatively low cytotoxicity, preferably providing less than 10%, preferably less than 2%, more preferably less than 0.05% cellular lethality in experiments as shown in Example 1 and compatibility with the assays described in Example 2;

(3) relatively low photobleaching in cells, as compared with dyes V, VI, IX–XII of Table 4, preferably less than 20%, more preferably less than 10%, most preferably less than 5% or undetectable photobleaching under conditions described in Example 1.

(4) relatively uniform spatial distribution in cells, as compared with dyes II–X of Table 4, preferably demonstrating negligible or no organelle accumulation, as demonstrated by confocal microscopy as performed in Example 1; in addition, time-resolved anisotropy measurements indicate that the majority of molecules of preferred compounds rotate freely and thus are not bound to cytoplasmic components; therefore, apart from their use as intracellular halide indicators, preferred compounds also provide excellent aqueous-phase probes for analysis of cytoplasmic rheology (Fushimi and Verkman, 1991) and comparative dye distribution;

(5) relatively high chemical stability in cells, as compared with SPQ; preferably providing less than 10%, preferably less than 2%, more preferably less than 0.5% degradation within a cell as described in Example 1 over one hour and during shelf storage over one year.

(6) relatively low leakage out of cells, as compared with SPQ; preferably less than 10%, more preferably less than 1%, most preferably less than 0.1% per hour in the cell system of Example 1; and (7) relatively rapid and efficient loading into cells, by a technique suitable to the compound, for example, by a brief hypotonic shock (e.g. 50% hypotonic medium for 3–5 min.), passive diffusion (e.g overnight incubation), microinjection, a reduction-oxidation strategy, etc., preferably loadable to at least 50%, more preferably at least 75%, most preferably at least 100% of the rapidity and efficiency of that of LZQ as demonstrated in Example 1.

In preferred embodiments, the compound has a molar extinction of $>6000M^{-1}cm^{-1}$ and a quantum yield of $>0.1$, preferably a molar extinction of $>10,000M^{-1}cm^{-1}$ and a quantum yield of $>0.25$, more preferably a molar extinction of $>20,000M^{-1}cm^{-1}$ and a quantum yield of $>0.5$. In a particular embodiment, the compound has an excitation wavelength of $>400$ nm and an emission wavelength of $>500$ nm.

Subject compounds may be covalently or non-covalently linked to a wide variety of other moieties, including chelators, targeting proteins, stabilizers, etc. In a particular embodiment, chemical modification and/or chromophore conjugation provide dual-wavelength indicators directly suitable for ratio imaging as would be required for measurements of I⁻ transport by cell cytometry, as described for the quinolinium-based Cl⁻ indicators (Jayaraman et al., 1999). Specifically, a second chromophore such as 6-aminoquinolinium is used as the I⁻ insensitive chromophore (favorable criteria include a red shifted emission spectra, a positively-charged heterocyclic nitrogen that prevents chromophore-chromophore interactions, and reversible reducibility to a cell-permeable dihydroquinolone). The chromophores are linked by various spacers including xylene and a long, rigid trans-1,2-bis(4-pyridyl)ethylene group. After loading into cells (e.g. using a reduction-oxidation strategy), intracellular anion concentration may be measured by computing the ratio of fluorescence signals determined at different emission wavelengths.

The cells of the subject methods are generally living cells, but may also include other membrane-bound vesicles such as reconstituted cells, including erythrocyte ghosts, synthetic cells including reconstituted liposomes and biomimetic phopspholipd vesicles (e.g. Chiu, et al. 1999), etc., preferably containing a functional anion transport protein or channel.

In particular embodiments, the method measures a change in fluorescence as a function of a predetermined condition such as the presence of a predetermined amount of a candidate modulator of ion transport in the cell (e.g. for drug screening) or the expression by the cell of a transgene, expression of which affects ion transport in the cell (e.g. to assess the efficacy of gene therapy in animal, e.g. MacVinish L J, et al. 1997a, or human, e.g. Example 2, studies. Preferred compounds find numerous applications in studies of CFTR gene delivery and drug screening. The use of SPQ has been problematic for CFTR transport in freshly isolated nasal or tracheal epithelial cells in gene therapy trials (Mansoura et al., 1999). The efficient incorporation of preferred compounds and their bright fluorescence in cells provides an attractive fluorescent indicator assay as a surrogate marker for CFTR gene delivery. The application of these compounds for measurement of CFTR-mediated halide transport using automated microplate reader technology establishes the basis for high-throughput drug screening. The correction of ΔF508 CFTR mistrafficking by low temperature, chemical chaperones (Brown et al., 1996), and other agents (Jiang et al., 1998) indicates that high potency modifiers of the CF phenotype are identifiable.

Anion transport measurements using fluorescent indicators are generally made on cell layers or individual cells grown or immobilized on a solid transparent support. Glass is a preferred support because of its strength, transparency and minimal autofluorescense, although some plastics are suitable. Surface coatings such as collagen or polylysine generally do not interfere with the measurement process. The cell layer on the transparent support is positioned on the stage of an epifluorescence microscope in a chamber designed for solution exchange to accomplish anion substitution, cAMP agonist addition, etc. A convenient approach is to grow cells on a round coverglass in a well of a 6 or 12-well plate. The coverglass is mounted in a closed chamber with the cells facing the solution and the cell-free surface facing the objective lens (details in Chao et al. (1989)). The thin coverglass permits viewing of the cells with a short working distance, high numerical aperture objective lens having efficient light collection. The cell layer is superfused continuously by gravity or a perfusion pump, and solution exchange is accomplished by a mechanical or electronic valve. Continuous perfusion is preferred to intermittent solution infusion to avoid pressure transients and convection artifacts, and to permit accurate temperature regulation. In addition, the accumulation of indicator that has leaked out of cells in a non-perfused system can produce an apparent increase in fluorescence signal that is not related to halide transport, particularly in the presence of low external solution halide concentration.

Other configurations may be used. Polarized epithelial cells can be grown on transparent, low-autofluorescent permeable supports and mounted in a double perfusion chamber in which the apical and basolateral cell surfaces are perfused independently. The details for construction of a double perfusion chamber are given in Verkman et al. (1992) with application to defining Cl⁻ transport mechanisms in airway epithelial cells. Transport measurements in cell suspensions by cuvette fluorimetry generally should be avoided because cells cannot be viewed directly. Fluorescence signals in a stirred cell suspension may arise from poorly viable cells and membrane fragments, as well as from indicator leakage out of cells.

Important applications of the disclosed compounds to measure halide transport include fluorescence activated cell sorting (FACS) and in vivo fiberoptic methods. For example, there are several strategies for measuring halide transport by flow cytometry by flow cytometry. After loading isolated cells in a suspension with a dual-wavelength halide indicator, cAMP-stimulated anion permeability may be determined by mixing cells with an anion-free solution at a fixed time before analysis by flow cytometry. The ratio of fluorescence signals provides a direct measure of anion efflux and thus of CFTR function. Another significant technological development is the in vivo measurement of halide transport using fiberoptics. Fiberoptics have been used extensively in the physical sciences for fluorescence-based sensors. Appropriately modified fiberoptic bronchoscopes are suitable for measurement of fluorescence by direct imaging methods or by total internal reflection.

A variety of light sources and detection methods are suitable for measurement of steady-state indicator fluorescence. The principal requirement for selection of a light source is stability. Stabilized arc lamps and lasers can be suitable light sources, but a superior choice is a simple incandescent lamp (e.g. tungsten-halogen lamp) powered by a stabilized direct current supply. Although incandescent lamps are relatively dim and emit with a red-shifted spectral content, they produce enough light to illuminate SPQ and other indicators at 350 nm. In order to minimize photobleaching and photodynamic cell injury, an important consideration is that the illumination intensity should be so low that the fluorescent cells are barely visible to the unaided eye. If necessary, neutral density filters can be introduced into the excitation light path to attenuate the light intensity. A photomultiplier, high gain photodiode, or low light level camera is required for detection. Photomultiplier and photodiode detectors are generally configured to detect an area-intergrated fluorescence signal arising from a small cluster of cells, whereas a camera detector typically records images for analysis of many individual cells, although area-integrated data analysis is feasible as well. Photomultipliers and photodiodes have a wide linear dynamic range; cooled charged coupled device (CCD) cameras (with 12-bit resolution and higher) also have a wide dynamic range, but silicon intensified target cameras and image intensifiers generally do not. Photomultiplier detection permits real-time data analysis with high signal-to-noise ratio and very low illumination intensities, such that continuous recordings can be made for an hour or longer without photobleaching or cell injury from illumination (Chao et al., 1989). Camera detection requires higher illumination intensities, intermittent image acquisition, and relatively complex data post-processing. However, as generally found in gene delivery studies, image detection provides information about cell heterogeneity that cannot be obtained by recording integrated fluorescence from many cells.

The subject compounds may be used to detect anion transport in a wide variety of cells and tissues; for example, Tables 1 and 2 summarize a number of applicable studies.

The invention also provides compounds and compositions which find a variety of applications, including use in the disclosed ion measuring methods and other methods involving luminescent detection, such as imaging, immunoassays, sequencing, etc. and in making compounds used in such methods. The subject compounds comprise the compounds described herein of the general formula I, with the proviso that the compound is other than 4-($\beta$-D-ribofuranosylamino)-pyrido [2,1-h] pteridin-11-ium-5-olate (LZQ) or 4-amino-pyrido [2,1-h] pteridin-11-ium-5-olate (LMQ); preferably wherein at least:

(a) one or more of the pairs $R_2$ and $R_3$, $R_3$ and $R_4$, $R_4$ and $R_5$, $R_6$ and $R_7$, and $R_8$ and $R_9$, may be directly or indirectly further covalently connected, to form a substituted or unsubstituted, aromatic or nonaromatic ring structure as described herein, (b) one or more of $R_2$–$R_7$ comprise a functional group, selected from a conjugation group, a polarity enhancing group an iodide sensitivity enhancing group as described herein, (c) $R_1$ is N, or (d) the compound is inside a cell as described herein.

TABLE 1

Cl⁻ Indicator Application to Study CFTR Function

| | CELL or TISSUE | | PROTOCOL | | |
|---|---|---|---|---|---|
| Findings/Significance | Cell Type | Description* | SPQ Loading | Quench Ion | Reference |
| CHARACTERIZATION OF CFTR EXPRESSING CELLS | | | | | |
| SPQ utility in normal and CF cells | Primary (1°) Culture | wt and CF ($\Delta$F/$\Delta$F) sweat duct cells | Passive 1–5 mM 2–24 hr. | Cl Br | (Ram and Kirk, 1989) |
| SPQ feasibility on polarized airway monolayers | 1° Culture | Canine tracheal epithelia | Hypotonic 5 mM 4 min. | Cl | (Verkman et al., 1992) |
| cAMP-dependent exocytosis in wt but not CF airway epithelia | 9HTEo⁻ | Transformed airway epithelia | Passive 5 mM 12 hr. | Cl | (Schwiebert et al., 1994) |
| Functional CFTR in endosomes | T84 Swiss 3T3 | Colon carcinoma Mouse embryo fibroblast | Passive 5 mM 2–18 hr. | Cl | (Biwersi et al., 1994) |
| Microplate assay for assessment of Cl transport | T84 CFPAC-1 | Colon carcinoma Pancreatic duct adenocarcinoma | Passive 10 mM, 12–18 hr | Cl | (West et al. 1996) |

TABLE 1-continued

Cl$^-$ Indicator Application to Study CFTR Function

| | CELL or TISSUE | | PROTOCOL | | |
|---|---|---|---|---|---|
| Findings/Significance | Cell Type | Description* | SPQ Loading | Quench Ion | Reference |

CHARACTERIZATION OF CFTR TRANSFECTED CELLS

| Findings/Significance | Cell Type | Description* | SPQ Loading | Quench Ion | Reference |
|---|---|---|---|---|---|
| Corrected CF phenotype by wt, but not ΔF508, CFTR cDNA | HeLa JME/CF15 1° culture | Cervical carcinoma (epithelial) Transformed CF airway epithelia Normal and CF airway epithelia | Passive 10 mM 12–18 hr. | Cl | (Rich et al., 1990) |
| Transfection of wt, but not ΔF508 CFTR cDNA induced cAMP-dependent Cl$^-$-transport | L cells | Mouse fibroblasts | Hypotonic 20 mM 4 min. | Cl | (Rommens et al., 1991) |
| Cl transport due to CFTR and not pre-existing Cl channels | L cells | Mouse fibroblasts | Hypotonic 20 mM, 4 min. | Cl | (Dho et al, 1993) |
| Transiently corrected CF phenotype with an adenoviral construct | CF-IBE | CF intrahepatic biliary epithelial | Hypotonic 4 min. | I | (Grubman et al., 1995) |
| CFTR trafficking to the plasma membrane was cAMP-dependent | HeLa | Cervical carcinoma (epithelial) | Hypotonic 10 mM 12 min. | I | (Howard et al., 1996b) |
| Transduction of AdCFTR induced cAMP-dependent Cl transport | 1° culture | Explant outgrowth model of normal and CF airway epithelia | Hypotonic 3.5 mM 10 min | Cl | (Dupuit et al., 1997) |

STRUCTURE-FUNCTION STUDIES OF CFTR MUTANTS

| Findings/Significance | Cell Type | Description* | SPQ Loading | Quench Ion | Reference |
|---|---|---|---|---|---|
| Identified 4 critical R domain serine residues which regulated CFTR via PKA phosphorylation | HeLa | Cervical carcinoma (epithelial) *Human cells expressing wt CFTR unless otherwise indicated. | Passive 10 mM 9–12 hr. | I | (Cheng et al., 1991) |
| Splice variants (Δexon5 and Δexon9) did not produce functional CFTR | HeLa | Cervical carcinoma (epithelial) | Passive 10 mM 9–12 hr. | I | (Delaney et al, 1993) |
| Serine-to-aspartate substitutions in the R domain mimicked PKA phosphorylation | HeLa | Cervical carcinoma (epithelial) | Passive 10 mM 12–18 hr. | I | (Rich et al 1993) |
| Deletion of J9 residues in the loop between TM4 and TM5 eliminated Cl transport | HBK 293-EBNA | Embryonic kidney cell line | Passive 5 mM 12–18 hr. | Cl | (Xie et al., 1995) |
| Coexpression of the N- and C-halves of CFTR resulted in functional Cl channels | HeLa | Cervical carcinoma (epithelial) | Passive 10 mM 12–18 hr. | I | (Ostedgaard et al., 1997) |

CORRECTION OF CF PHENOTYPE BY PHARMACOLOGICAL INTERVENTION

| Findings/Significance | Cell Type | Description* | SPQ Loading | Quench Ion | Reference |
|---|---|---|---|---|---|
| Increased [IBMX] improved ΔF508 response; Reduced temp. improved ΔF508 and G551D | L cells | Mouse fibroblasts | Hypotonic 12 hr. | I | (Yang et al., 1993) |
| Transfer of purified CFTR protein induced Cl transport | CHO-CFTR FRT-CFTR LLCPK1 | Chinese hamster ovary Fisher rat thyroid epithelial Pig kidney epithelial | Passive 10 mM 12–18 hr. | I | (Marshall et al., 1994) |
| Overexpression of ΔF508 with sodium butyrate resulted in detectable Cl transport | CFPAC-1 JME/CF15 1° culture | Pancreatic duct adenocarcinoma (ΔF/ΔF) Transformed CF airway epithelial CF airway epithelial | Passive or Hypotonic 10 mM | I | (Cheng et al., 1995) |
| Chemical chaperones (glycerol, D$_2$O, TMAO) corrected the CF phenotype | Swiss 3T3 | Mouse embryo fibroblast | Passive 5 mM 12–18 hr. | Cl | (Brown et al., 1996) |
| Aminoglycoside antibiotics overcame premature stop codons and corrected CF phenotype | HeLa | Cervical carcinoma (epithelial) | Hypotonic 10 mM 10 min. | I | (Howard et al., 1996a) |
| Deoxyspergualin delivered ΔF508 to plasma membrane and partially restored Cl transport | C127-CFTR JME/CFI5 IBE-1 | Mouse mammary epithelial Transformed CF airway epithelial Transformed intrahepatic (ΔF/G542X) | Hypotonic 10 mM. 4 min. | I | (Jiang el al., 1998) |

TABLE 2

Cl$^-$ Indicator Application to Study CFTR Delivery in Human Clinical Trials

| Findings/Significance | Cell Source | Method of Gene Transfer | CFTR cDNA promoter | # of days post-transfer | SPQ loading | Reference |
|---|---|---|---|---|---|---|
| Utility of SPQ in freshly isolated epithelial cells. | Normal, CF nasal epithelia Normal bronchial epithelia | — | endogenous | — | Hypotonic 10 mM 4 min. | Stern et al., 1995 |
| Established protocols for gene therapy trials | Normal and CF nasal epithelia | — | endogenous | — | Hypotonic 10 mM 4 min. | McLachlan etal, 1996 |
| No detectable changes from pre-treatment or vs. placebo | Normal and CF nasal epithelia | Lipid-mediated (DC-Chol/DOPE) | CMV | 7 days | Hypotonic 10 mM 4 min. | Porteous et al., 1997 |

TABLE 2-continued

Cl⁻ Indicator Application to Study CFTR Delivery in Human Clinical Trials

| Findings/Significance | Cell Source | Method of Gene Transfer | CFTR cDNA promoter | # of days post-transfer | SPQ loading | Reference |
|---|---|---|---|---|---|---|
| Detectable Cl transport after CFTR cDNA transfer in ~50% of patients | CF nasal epithelia | Lipid-mediated (DC-Chol/DOPE) | RSV 3'LTR | 3–4 days | Hypotonic | Gill et al., 1997 |

All studies used iodide as the quenching ion and 20–25 $\mu$M Forskolin + 100 $\mu$M IBMX as the cAMP agonists. Two of the studies (McLachlan et al., 1996; Porteous et al., 1997) also added 0.5 mM cAMP.

TABLE 3

Buffer compositions and protocols for perfusion experiments

| protocol | buffer #1 | buffer #2 | buffer #3 | buffer #4 |
|---|---|---|---|---|
| 1 | PBS + forskolin (20 $\mu$M) | buffer A (100 mM I⁻) + forskolin (20 $\mu$M) | 150 mM KSCN | |
| 2 | buffer A (100 mM I⁻) | PBS | PBS + cAMP stimulation | 150 mM KSCN |
| 3 | PBS | buffer D (50 mM I⁻) | PBS | buffer B (50 mM I⁻) |
| 4 | buffer C (20 mM I⁻) | buffer C (NO₃⁻) | buffer D (NO₃⁻) + cAMP stimulation | 150 mM KSCN |
| 5 | buffer D (NO₃⁻) + cAMP stimulation | buffer C (20 mM I⁻) + cAMP stimulation | 150 mM KSCN | |
| 6 | PBS + forskolin (20 $\mu$M) | buffer D (NO₃⁻) + forskolin (20 $\mu$M) | 150 mM KSCN | |
| 7 | buffer D (NO₃⁻) | buffer D + water (3:1) | buffer D NO₃⁻ | buffer D + 150 mM NaNO₃⁻ |

Buffer compositions are as follows:
PBS: 137 mM NaCl, 2.7 mM Kcl, 0.9 mM CaCl₂, 0.5 mM MgCl₂, 8 mM Na₂HPO₄, 1.5 mM KH₂PO₄.
Buffer A: 100 mM NaI, 37 mM NaCl, 2.7 mM Kcl, 0.9 mM CaCl₂, 0.5 mM MgCl₂, 8 mM Na₂HPO₄, 1.5 mM KH₂PO₄.
Buffer B: 50 mM NaI, 87 mM NaCl, 2.7 mM Kcl, 0.9 mM CaCl₂, 0.5 mM MgCl₂, 8 mM Na₂HPO₄, 1.5 mM KH₂PO₄.
Buffer C: 20 mM NaI, 117 mM NaNO₃, 2.7 mM KNO₃, 0.9 mM Ca(NO₃)₂, 0.5 mM Mg(NO₃)₂, 8 mM Na₂HPO₄, 1.5 mM KH₂PO₄.
Buffer D: 137 mM NaNO₃, 2.7 mM KNO₃, 0.9 mM Ca(NO₃)₂, 0.5 mM Mg(NO₃)₂, 8 mM Na₂HPO₄, 1.5 mM KH₂PO₄.

TABLE 4

Optical and cellular properties of some analyzed compounds

| No. | Compound name | $\lambda_{ex}$ (nm) | $\lambda_{em}$ (nm) | $K_{sv}$ (I⁻) (M⁻¹) | Brightness | Cellular properties |
|---|---|---|---|---|---|---|
| I | luminarosine | 424 | 528 | 60 | +++ | staining uniform; leakage rate very low; slow photobleaching |
| II | luminarine | 424 | 530 | 70 | +++ | staining uniform; leakage rate moderate; slow photobleaching |
| III | rhodamine-110 | 496 | 520 | 40 | ++++ | accumulates in mitochondrial compartments |
| IV | rhodamine green | 505 | 530 | 30 | ++++ | accumulates in mitochondrial compartments |
| V | 1-methyl-benzo{c}cinnolinium | 416 | 505 | 130 | ++ | uniform cytoplasmic staining but stains nucleus also; photobleached rapidly |
| VI | 1-methyl-phenazinium | 440 | 520 | 90 | ++ | strong nuclear staining; photobleached rapidly |
| VII | 1-methyl-2,7-diphenylpyrido-[3,2,g]quinolinium | 405 | 515 | 46 | +++ | uniform cytoplasmic staining but also stains nucleus |
| VIII | resorufin | 571 | 585 | 76 | +++ | accumulates in intracullular vesicles |
| IX | 10-methyl acridinium yellow | 440 | 520 | 90 | ++++ | strong nuclear staining; very rapid photobleaching |
| X | 10-methyl acridinium orange | 440 | 550 | 30 | ++++ | strong nuclear staining; very rapid photobleaching |
| XI | 6-amino-1-(3-sulfopropyl) quinolinium | 396 | 545 | 240 | + | uniform cytoplasmic staining; rapid photobleaching |
| XII | 9-amino-10-(3-sulfopropys) acridinium | 422 | 457 | 253 | +++ | nuclear staining; rapid photobleaching |
| XIII | phenosafranine | 520 | 586 | 33 | ++ | accumulates in intracelular vesicles |

$\lambda_{ex}$: exitation wavelength, $\lambda_{em}$: emission wavelength, $K_{sv}$: Stern Volmer quenching constant.
++++ very bright; +++ bright; ++ moderate brightness; + weak TABLE 5
Chemical structures of indicators (see Table 4 for compound names and properties).
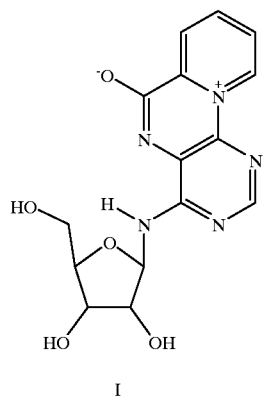
I
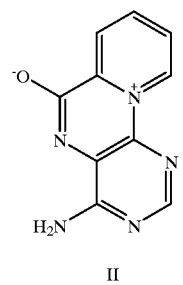
II
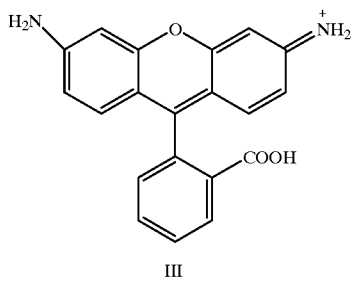
III
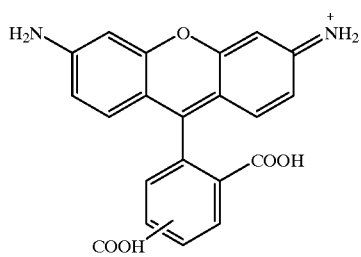
IV
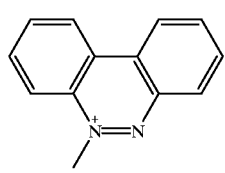
V
TABLE 5-continued
Chemical structures of indicators (see Table 4 for compound names and properties).
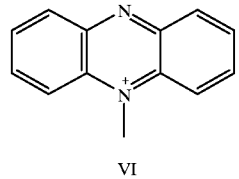
VI
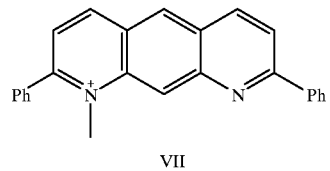
VII
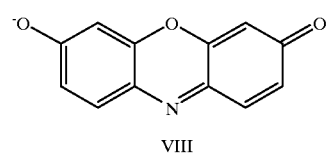
VIII
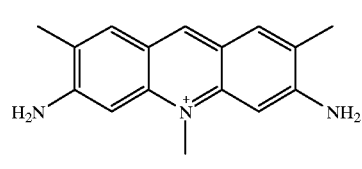
IX
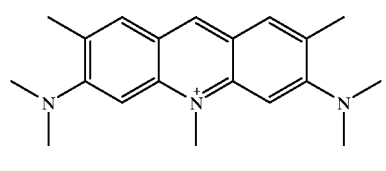
X
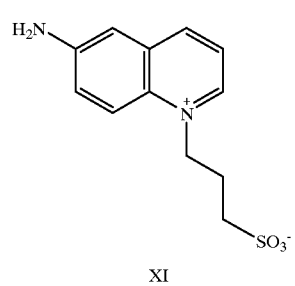
XI
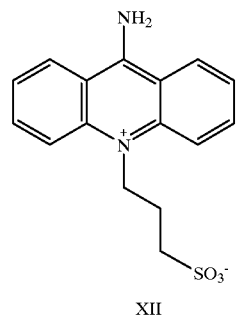
XII TABLE 5-continued Chemical structures of indicators (see Table 4 for compound names and properties).

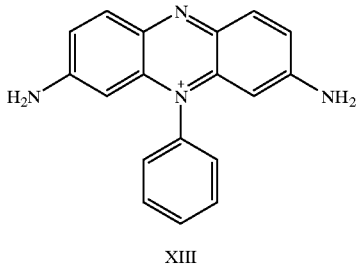

XIII

EXAMPLES

Example 1

Characterization of Exemplary Long-wavelength Iodide-sensitive Fluorescent Indicators for Measurement of Anion Transport in Cells.

Materials. Forskolin, 8-(4-chlorophenylthio)adenosine-3',5'-cyclic monophosphate sodium salt (CPT-cAMP), 3-isobutyl-1-methylxanthine (IBMX), nigericin, valinomycin and carbonyl cyanide-m-chlorophenylhydrazone (CCCP) were purchased from Sigma (St. Louis, Mo.). Rhodamine 110 and rhodamine green were purchased from Molecular Probes (Eugene, Oreg.). Acridine yellow, acridine orange, 9-aminoacridine, 6-aminoquinoline, benzo[c]cinnoline, phenazine, resorufin and phenosafranine were obtained from Aldrich (Milwaukee, Wis.).

Organic synthesis. Benzo[c]cinnoline and phenazine were quaternized with methyl iodide to give compounds V and VI, respectively (see Table 5 and Table 3). Compound VII was synthesized by reaction of 2,7-diphenylpyrido[3,2-g]quinoline with trimethyloxonium tetrafluoroborate. Acridine yellow and acridine orange were quaternized with dimethyl sulphate to give compounds IX and X, respectively. 6-aminoquinoline and 9-aminoacridine were quaternized with propane sultone to give compounds XI and XII, respectively. Compounds I (LZQ) and II (LMQ) were synthesized by phototransformation of N-[9-(2',3',5'-tri-O-acetyl-b-D-ribofuranosyl)-purin-6-yl]pyridinium chloride in aqueous solutions (Skalski et al., 1987, 1989). Briefly, 2',3',5'-tri-O-acetylinosine was reacted with 4-chlorophenyl dichlorophosphate in pyridine. The resulting N-[9-(2',3',5'-tri-O-acetyl-b-D-ribofuranosyl)purin-6-yl]pyridinium chloride was converted quantitatively into intermediate N-[5-formamido-6-[(2',3',5'-tri-O-acetyl-b-D-ribofuranosyl)amino] pyrimidyn-4-yl]pyridinium chloride by irradiation of a deoxygenated aqueous solution (0.2 mM) at pH 6–6.3 with near UV light (1>300 nm). After completion of the photoconversion reaction, solution pH was raised to 7.5 with saturated aqueous NaHCO$_3$ followed by addition of N-(9-methylpurin-6-yl)-pyridinium perchlorate (1.5 molar equivalents). The irradiation was continued, yielding a bright yellow solution which was extracted with chloroform to give 2',3',5'-tri-O-acetylluminarosine. LZQ was prepared by de-O-acetylation of 2',3',5'-tri-O-acetylluminarosine in absolute methanol with triethylamine at room temperature for 72 h. LMQ was prepared by heating 2',3',5'-tri-O-acetylluminarosine in 0.1 M aqueous trichloroacetic acid to 90° C. for 3 h.

Cell culture. For fluorescence microscopy experiments, 3T3 fibroblasts (control and CFTR-expressing), T84 cells and Calu-3 cells were cultured on 18 mm round coverslips in DME H21 medium supplemented with 5% fetal calf serum (3T3 fibroblasts) or 10% fetal calf serum (Calu-3 cells), penicillin (100 U/ml) and streptomycin (100 mg/ml). T84 cells were grown in DMEM/F-12, Ham's nutrient mix (1:1) containing 5% fetal calf serum, penicillin (100 U/ml) and streptomycin (100 mg/ml). Cells were grown at 37° C. in 95% air, 5% $CO_2$ and used when 90% confluent. For microplate reader assays cells were cultured on Costar 96-well black plates with a clear flat bottom and used when nearly confluent.

Fluorescence microscopy. Fluorescence microscopy measurements were performed as described previously (Chao et al., 1989). Briefly, coverglasses were mounted in a 0.5 ml perfusion chamber in which the cell-free glass surface made contact with an oil immersion objective (Nikon ×40 magnification, numerical aperture[NA] 1.3). Cell fluorescence was excited at 365±10 nm (SPQ) or 420 nm±10 nm (LZQ and LMQ). Emitted fluorescence was detected by a photomultiplier in a Nikon inverted epifluorescence microscope using a 410 nm dichroic mirror and 420 nm barrier filter (SPQ) or a 455 nm dichroic mirror and 500 nm barrier filter (LZQ). For cells colabeled with SPQ and LZQ, SPQ fluorescence was excited at 365±10 nm and detected using a 410 nm dichroic mirror and 455±30 nm interference filter. Confocal fluorescence micrographs were obtained using a Nipkow wheel confocal microscope and cooled CCD camera detector using a ×60 oil immersion objective (Nikon, NA 1.4). LZQ-labeled cells were viewed using a fluorescein filter set (excitation 480±15 nm, emission 520±20 nm).

Fluorescence microplate reader measurements. Microplate reader measurements were performed in a BMG Fluostar microplate reader (BMG LabTechnologies Inc., Durham, N.C.) equipped with two syringe pumps for automated solution additions. After cell loading with LZQ, extracellular LZQ was washed using a Labsystems Cellwash-4 (Franklin, Md.). LZQ fluorescence was excited using a liquid fiberoptic and 405±20 nm interference filter, and emitted fluorescence was collected using a liquid fiberoptic and 538±12 nm filter. The fiberoptic was positioned just below the plate. Fluorescence was recorded continuously in 2 s intervals, each representing the average of one hundred 20-ms pulses of the Xenon illumination lamp source.

Transport measurements. Table 3 lists the solution compositions and protocols for the transport measurements. Cells were labeled with LZQ or SPQ by hypotonic shock (loading buffer/water 1:1 containing 2 mM LZQ or 7.5 mM SPQ) for 5 min at room temperature or by overnight incubation with indicators in the cell culture medium. Extracellular indicator was removed by washing just prior to measurements. For fluorescence microscopy, glass coverslips were then mounted in a perfusion chamber (flow ~2 ml/min) in which solutions were exchanged using a 4-way valve. For microplate reader measurements, cells in 96-well plates were bathed in 20 ml of the '1st buffer' (see Table 3) and 160 ml of the Cl$^-$-containing, I$^-$-free solution was injected into the well to drive Cl$^-$/I$^-$ exchange (protocol 1). For stimulation of CFTR using protocol 2, 60 ml of a 1:8 mixture of the 1st buffer and the 2nd buffer containing 80 mM forskolin, 2 mM CPT-cAMP and 400 mM IBMX was added.

Time resolved fluorescence measurements. Fluorescence lifetime and anisotropy decay measurements were carried out in the frequency domain by cuvette fluorimetry using a Fourier transform fluorimeter (48000 MHF, SLM Instruments, Urbana, Ill.) or by fluorescence microscopy using epifluorescence microscope optics in place of the cuvette compartment (Verkman et al., 1991). For microscopy measurements, impulse-modulated vertically polarized light (442 nm, He—Cd laser 35 mwatts) was reflected onto the sample by a 510 nm dichroic mirror and objective lens; emitted fluorescence was filtered by a 515 nm barrier filter and passed through a rotatable analyzing calcite polarizer. In some experiments, a biconcave lens was introduced just in front of the dichroic mirror to diverge beam diameter in the focal plane to ~40 mm.

Analysis of lifetime and time-resolved anisotropy was performed by a comparative approach. Generally six pairs of measurements (each acquisition 8 s) were obtained, comparing sample and reference (fluorescein in 0.1 N NaOH, lifetime 4.0 ns) for measurement of lifetime, and parallel and perpendicular orientations of the emission polarizer for measurement of anisotropy decay. The phase-modulation data consisted of phase angles and modulation ratios at 40 discrete, equally spaced modulation frequencies (5–200 MHz). The analyzing polarizer was positioned at the magic angle for lifetime measurements. Additional details of the data acquisition and analysis routines were described previously (Verkman et al., 1991). Median phase and modulation values for paired data were analyzed by nonlinear least-squares for determination of lifetimes and rotational correlation times.

Computations. In vitro fluorescence quenching studies were carried out at peak excitation and emission wavelengths. Microliter aliquots of the sodium salt of the quenching anion (1 M) were added to indicator solution in 5 mM sodium phosphate (pH 7.2, unless indicated otherwise). Fluorescence intensities in the absence ($F_o$) and presence (F) of quencher anion ([Q]) were measured to give the Stem-Volmer constant ($K_q$) as defined by:

$$F_o/F = 1 + K_q[Q].$$

For determination of the absolute $I^-$ transport rates, the time course of intracellular $[I^-]$ was computed from the time course of SPQ or LZQ fluorescence using the modified Stem-Volmer equation $[I^-] = \{([F_o - F_b]/[F - F_b]) - 1\}/K_f$, where $F_o$ is fluorescence intensity in the absence of $I^-$, $F_b$ is background fluorescence of unlabeled cells, and $K_f$ the intracellular quenching constant for $I^-$ (see Results). $I^-$ transport rates were calculated from the slope of a linear regression of the first 10 time points after changing perfusate composition.

Results. Long-wavelength fluorophores were screened for sensitivity to $Cl^-$ and $I^-$, and intracellular properties (loading, intracellular distribution, leakage, stability). Table 3 summarizes the optical and cellular properties of some of the fluorophores tested. The available $Cl^-$ indicators are based on fluorescence quenching of the quinolinium chromophore and similar positively-charged heterocycles. Various classes of compounds were tested with extended conjugation, one or more heteroatoms, and linear or angular geometry. Several rhodamines were tested based on reports indicating rhodamine sensitivity to $I^-$ (Wyatt et al., 1987). Although several of the compounds tested showed good sensitivity to $Cl^-$ (compounds V, VI) and $I^-$ in vitro, they were not useful as intracellular indicators because of instability, non-uniform intracellular distribution, and/or rapid leakage out of cells as given in Table 4. Of the compounds tested, the pyrido[2,1-h]-pteridins LZQ and LMQ had potentially useful optical and cellular properties and were characterized further.

Fluorescence spectra reveal that LZQ and LMQ have broad excitation and emission peaks with maxima at 424 and 528 nm, respectively. The molar extinction coefficient of LZQ was 11,100 $M^{-1}cm^{-1}$ at 424 nm and the quantum yield in the absence of $I^-$ was 0.53. Stem-Volmer plots for quenching of LZQ and LMQ by $I^-$ and $Cl^-$, with data for SPQ shown for comparison, were generated. In water (or saline), LZQ fluorescence was quenched by $I^-$ with a Stem-Volmer constant of 60 $M^{-1}$. LZQ fluorescence was not quenched (Stem-Volmer constant <1 $M^{-1}$) by $Cl^-$, $NO_3^-$, phosphate, acetate, $Na^+$ and $K^+$. LZQ fluorescence and $I^-$ sensitivity were not affected by pH changes in the range 4.5–8. Fluorescence lifetime analysis indicated a 7.1 ns lifetime for LZQ in the absence of I- which decreased in proportion to fluorescence intensity with increasing $[I^-]$, indicating a collisional mechanism. Stopped-flow measurements showed that LZQ fluorescence responds in <1 ms to rapid addition and removal of $I^-$, as expected for a collisional quenching mechanism.

LZQ and LMQ were loaded into cells efficiently by hypotonic shock or passive incubation. Confocal fluorescence micrographs showed LZQ fluorescence labeling of the aqueous compartments in cytoplasm and nucleus. The green/yellow LZQ fluorescence was quite uniform and remarkably more intense than the blue fluorescence of SPQ, even though a substantially higher SPQ concentration was used. All cell types tested, including epithelial cells (T84, Calu-3, JME, LLC-PK1, MDCK) and non-epithelial cells (3T3 fibroblasts, CHO cells, HeLa cells) could be labeled with LZQ and showed uniform labeling of the cytoplasm and nucleoplasm. As was found for SPQ, LZQ and LMQ were non-toxic to cells in assays of cell growth (2 mM in culture medium for 72 h). Thin layer chromatography of lysates from LZQ-loaded cells showed that LZQ remained chemically stable in cells.

It was found that LZQ had better cytoplasmic retention properties than LMQ, probably because of its sugar moiety. A time course of LZQ fluorescence during perfusion with physiological saline at 23° C. was generated. A small group of 20–30 cells was illuminated continuously and fluorescence was detected by a photomultiplier using an ×40, 1.3 NA objective. Cellular fluorescence decreased slowly at a rate of 2.5% per hour. To determine the relative contributions of indicator leakage vs. photobleaching to the slow decline in fluorescence, the perfused cells were illuminated intermittently. The decline in fluorescence was not different from that during continuous illumination, indicating the absence of photobleaching under the low light level conditions employed here. A time course of cellular LZQ fluorescence in response to repeated addition and removal of 50 mM $I^-$ revealed large, reversible changes in fluorescence with signal-to-noise ratios generally better than 500-to-1. Background fluorescence (in non-labeled cells) was generally <5% of the fluorescence of LZQ-labeled cells.

A calibration study was done to determine the intracellular sensitivity of LZQ to $I^-$. 3T3 fibroblasts expressing CFTR were perfused with solutions containing high $[K^+]$ and ionophores to equalize solution and intracellular $[I^-]$. LZQ fluorescence changed reversibly in response to changes in solution $I^-$. A Stem-Volmer analysis indicated a Stem-Volmer constant of 26 $M^{-1}$ for quenching of intracellular LZQ by $I^-$, which is better than that of 12–18 $M^{-1}$ for quenching of intracellular SPQ by $Cl^-$ (Chao et al., 1989). Fluorescence lifetime analysis was done to determine whether LZQ fluorescence is quenched in cells by substances other than $I^-$. Nanosecond lifetimes were measured by frequency-domain microfluorimetry. A phase-modulation plot indicated a single-component LZQ lifetime in cells of 6.5±0.3 ns (n=4) in the absence of $I^-$, close to that of 7.1 ns for LZQ in water. This finding contrasts with results for SPQ, where the SPQ fluorescence lifetime was 8-fold decreased in cells (in the absence of Cl⁻) vs. water (Chao et al., 1989). It is concluded that LZQ fluorescence is quenched little by intracellular components, a significant advantage over SPQ.

The similar LZQ lifetime in cells and water predicts that LZQ fluorescence should be relatively insensitive to cell volume in the absence of I⁻. A comparison of the time course of intracellular SPQ and LZQ fluorescence in response to osmotically-induced changes in cell volume in the absence of Cl⁻ revealed that whereas SPQ fluorescence decreased by 30±2% (S.E., n=3) upon exposure to 600 mOsm, LZQ fluorescence changed by only 5±1% (in the absence of I⁻). When cells were exposed to hypoosmotic medium (225 mOsm), SPQ fluorescence increased by 15±2%, whereas LZQ fluorescence increased by only 4±1%.

The uniform cellular distribution of LZQ indicates that LZQ is in the aqueous phase of cytoplasm and nucleoplasm, and binds little to intracellular proteins and lipids. Time-resolved anisotropy was measured to quantify intracellular LZQ binding. In water, LZQ rotated freely with a single-component rotational correlation time of 121±3 ps (n=3). For LZQ in cells, a plot of differential phase and modulation amplitude ratio indicated a two-component anisotropy decay model with a major component (fractional amplitude 0.90–0.94) of 144±10 ps, similar to that in water. Together these results indicate negligible binding of LZQ to intracellular components.

The utility of LZQ for functional measurement of CFTR expression was tested. A comparison of the time course of LZQ and SPQ fluorescence in forskolin-stimulated CFTR-expressing cells using identical I⁻/NO₃⁻ exchange protocols revealed that although the amplitudes and curve shapes of the data differed for SPQ vs. LZQ because of unequal indicator Stein-Volmer constants, the computed I⁻ influx rates (SPQ: 0.26±0.03 mM/s; LZQ: 0.25±0.01 mM/s, S.E., n=3) and efflux rates (SPQ: 0.08±0.01 mM/s; LZQ: 0.09±0.03 mM/s) were not different. A comparison of data obtained for cells loaded with LZQ and SPQ initially loaded with I⁻, followed by replacement of I⁻ with NO₃⁻ in the absence of forskolin, followed by addition of forskolin was also performed. The initial rates of forskolin-stimulated I⁻ efflux (SPQ: 0.09±0.02 mM/s; LZQ: 0.08±0.01 mM/s) were similar. Measurements of Cl⁻/NO₃⁻ exchange were also carried out by measuring SPQ fluorescence using cells labeled with SPQ alone vs. cells colabeled with SPQ and LZQ. The presence of LZQ (which is quenched by I⁻ but not by Cl⁻) did not affect the time course of SPQ fluorescence, indicating that LZQ did not itself affect CFTR-mediated Cl⁻ transport.

Because LZQ fluorescence is sensitive to I⁻ but not to Cl⁻, it was possible to measure Cl⁻/I⁻ exchange without the need to introduce NO₃⁻. The kinetics of forskolin-stimulated Cl⁻ efflux upon replacement of solution Cl⁻ by I⁻ measured by LZQ fluorescence was examined. A rapid decrease in LZQ fluorescence was seen in the CFTR-expressing fibroblasts and T84 cells, but not in control fibroblasts. Measuring cAMP-stimulated I- efflux in response to replacement of solution I⁻ by Cl⁻ and addition of cAMP agonists revealed that there was a slow increase in fluorescence upon solution exchange, representing basal anion transport, followed by a prompt increase in LZQ fluorescence upon addition of cAMP agonists to the CFTR-expressing cell types.

The low rate of LZQ leakage out of cells and its bright long-wavelength fluorescence permitted measurements of CFTR-mediated Cl⁻/I⁻ or NO₃⁻/I⁻ exchange in a fluorescence microplate reader with cells cultured directly on 96-well plastic dishes. To establish a protocol for the microplate reader assay, the background fluorescence of clear flat bottom, 96-well plates obtained from different vendors was measured at LZQ excitation and emission wavelengths. Fluorescence signals (in instruments units±SD[to assess inter-well variability] at gain typically used in transport assays) were: 12258±386 (Falcon clear), 9749±568 (Nunc clear), 23167±755 (Greiner white), 39782±555 (Falcon white), 8955±116 (Packard Polyfibronics black), 9582±211 (Falcon black), 6989±192 (Nunc black), 6420±562 (Greiner black), 5068±268 (Costar black). Costar black plates were used for subsequent studies because of their relatively low background signal and inter-well variability. Background fluorescence was generally 5–10 fold lower than cellular LZQ fluorescence, with very little (<2%) instrument background (with 96-well plate removed) or cellular autofluorescence (measured in unlabeled cells). Another technical consideration was selecting the flow rate and fluid volume added by the syringe pumps to adapt the microscopy protocol to the microplate reader. Exchange of I⁻ for Cl⁻ was effected in the microplate reader by diluting the I⁻ containing buffer with a Cl⁻ buffer. In order to minimize rapid signal changes due to a rise in meniscus level and the associated light scattering, cells were initially bathed in a minimum 20 ml volume of the "1st buffer" (Table 3) and diluted with 160 ml of the "2nd buffer". The rates of fluid addition by the automated syringe pump was maintained at 150 ml/s in order to avoid bubbles (causing light scattering) and displacement of the cells from the flat-bottomed plastic well.

cAMP-stimulated CFTR-mediated transport was also readily detected in microplate reader format assays. Cells were loaded with 2 mM LZQ by a 5 min hypotonic shock and extracellular LZQ was removed by rinsing the wells. Protocols 1 and 2 (Table 3) were compared for measurement of CFTR-stimulated I⁻ transport. Resultant microplate reader data shows rapid I⁻ influx in the CFTR-expressing fibroblasts and T84 cells, but not in control fibroblasts. The data also show cAMP-stimulated I⁻ efflux in T84 cells, but not in a cell line (JME) expressing the DF508 CFTR.

Example 2

Use of Halide Indicators to Evaluate Liposome-mediated Gene Transfer to the Nasal Epithelium of Patients with Cystic Fibrosis.

Subjects. Twelve CF patients (eight male and four female) with defined CF genotypes are enrolled in the study. All patients are over 16 years of age and give written informed consent. The patients continue with their normal treatment during the 4-week study.

Study design. In addition to the routine clinical examination at each visit, patients are asked to report any symptoms. The subjects are randomly assigned a treatment regimen, such that both patients and investigators are blinded to the treatment each subject receives, and remain blinded until after completion of data analysis.

Gene transfer reagents. Two plasmids, pTRIAL10 and pTRIALCFTR2 are used in this study (MacVinish L J et al. 1997b). Both plasmids contain an expression unit consisting of the RSV 3'LTR promoter and the late polyadenylation signal from simian virus 40; and the tetracycline-resistance gene incorporating a mutation to minimize expression in mammalian cells. The plasmids are identical except that pTRIAL10CFTR2 contains the human CFTR cDNA. This plasmid is shown to express functional CFTR protein in cells grown in vitro and in an animal model. Plasmid DNA is prepared at the Imperial Cancer Research Fund's Biotherapeutics and Hybridoma Development Unit in London.

The plasmid DNA is supplied sterile and essentially free of endotoxins (<1 EU/mg DNA), in single-use vials at a concentration of 0.667 mg/ml in Kreb's HEPES buffer (pH 9.0).

DC-Chol/DOPE cationic liposomes are prepared under conditions approved by the US Food and Drug Administration (Gao X, et al. 1991). The DC-Chol/DOPE liposomes (6:4 molar ratio of DC-Chol to DOPE) were made by a microfluidization procedure, to a final concentration of 2 µmol/ml (equivalent to 1.2 mg/ml of total lipid) in endotoxin-free water (Sorgi F L, et al. 1997). The transfection efficiency of the liposomes is assayed using HeLa cells and a plasmid expressing the chloramphenicol acetyl transferase reporter gene (MacVinish L J et al. 1997b). The DNA and liposomes are equilibrated to room temperature and mixed approximately 5 min before patient administration.

Dosing. Four treatment regimens are compared in the trial. To ensure that the absolute concentration of DNA-liposomes is equivalent in each dose, different volumes of the gene transfer reagents is administered. Four patients receive a low CFTR dose, such that each nostril receives 0.8 ml containing 40 µg pTRIAL10 CFTR2 DNA complexed with 0.4 µmol DC-Chol/DOPE. Four patients receive a high CFTR dose (8 ml) containing 400 µg pTRIAL10 DNA complexed with 4 µmol DC-Chol/DOPE. Two patients receive control vector dose (8 ml) containing 400 µg pTRIAL10 DNA complexed with 4 µmol DC-Chol/DOPE and two patients receive Kreb's HEPES Buffer (0.8 ml). The last two regimens constituted the placebo doses.

The treatment solutions are delivered to the patients in four sessions spread over 2 days, such that a quarter of the total dose (0.2 ml or 2.0 ml as appropriate) is administered at each treatment session. The treatment solutions are instilled directly on to the nasal septum using an MS16A syringe driver from Graseby Medical (Watford, UK) via a soft, infant, 4F, 50 cm feeding catheter from Portex (Hythe, UK). The patients lie on their left side with their head tilted down and the tube is placed 2 cm into the right nostril. The solution is delivered over a period of 15 min following which the patient remains in the same position for a further 15 min. After sitting upright for a few minutes, the patient is repositioned on their right side to instil the dose into the left nostril. Radioisotope studies demonstrate that while maximizing the delivery to the nasal septum, this method gives a good spread of solution (using both 0.2 ml and 2.0 ml volumes) throughout the nasal cavity with minimal mucociliary clearance into the nasopharynx over 30 min.

Nasal biopsy. An epithelial biopsy is taken from the left nostril of each patient 6 days after dosing (day 15). The biopsy is taken using local anesthesia. Cotton wool soaked with 5% cocaine solution is placed in the left nostril for 5 min. Cocaine paste (25%) is then applied directly to the nasal septum. The biopsy (3–5 mm$^2$) is taken approximately 3 cm back from the anterior nares on the nasal septum, the site of maximal exposure to the treatment solution. Histology of this region from control individuals reveals both transitional and ciliated, respiratory epithelia. The tissue is stored in formalin fixative and the tissue processed and stained with hematoxylin and eosin for histological examination. Adjacent sections are immunostained with peroxidase-labelled monoclonal antibodies against either neutrophil elastase (By87a; anti-neutrophil elastase), T cells (CD3; anti-CD3), B cells (JCB117; anti-CD79a) or macrophages (PGM1 or KP1; anti-CD68) according to standard pathology procedures and examined for evidence of inflammation.

Ex vivo electrophysiological measurements (halide indicator analysis). CFTR function is assessed in freshly isolated, nasal epithelial cells collected from the region between the middle and inferior turbinates by gentle brushing with a 3 mm cytology brush. Both nostrils are brushed and the cells from each nostril combined. A proportion of the resulting cell suspension consists of ciliated epithelial cells which we and others have shown to possess ion transport properties characteristic of the airway epithelium (Stem M. et al. 1995). Cells are loaded with the halide-sensitive fluorophore 4-(β-D-ribofuranosylamino)-pyrido[2,1 -h]-pteridin-11-ium-5-olate (LZQ) by hypotonic shock. Halide efflux stimulated by the addition of 100 µm 3-isobutyl-1-methyl-xanthanine (IBMX) and 25 µm forskolin (Fsk) from Sigma Chemical (Poole, UK) is measured essentially as described in Stem M. et al. 1995. In the presence of functioning CFTR protein, the addition of cAMP agonists results in a reduction in the intracellular halide concentration. This reduction can be measured by an increase in LZQ fluorescence. Fluorescence images (excitation 350 nm, emission >430 nm) of the cells are captured every 30 s using Leica DMIRBE fluorescence microscope (Milton Keynes, UK) in conjunction with an Intracellular Ion Imaging System from Improvision (Coventry, UK). Studies are at room temperature. Wherever possible the cell sample is divided and one half used as a negative control in which the cAMP agonists are omitted. Where insufficient cells are obtained for division of the sample, the cells are subjected to the experimental conditions only. Fields of cells (typically 25–500 cells) are visualized at ×100 magnification. The brightest regions of interest are selected for quantification of fluorescence from the last image without knowledge of the rate of fluorescence change. The number of regions of interest analyzed for each individual varies between 20 and 100. To correct for cell-to-cell differences in absolute fluorescence intensity (due to differences in cellular concentration of LZQ, cell size and cell clumping) the data are presented as percentage relative intensity which is $100 \times (F_t/F_o)$ where $F_t$ is fluorescence intensity at time t and $F_o$ is the mean of fluorescence intensity for the initial 120 s.

In vivo eletrophysiological measurements (PD analysis). CFTR function is assessed in vivo by measuring the potential difference (PD) across the nasal epithelium on the floor of the nasal cavity on 11 occasions during the study. Measurements are performed essentially as described (Middleton P G, Geddes D M, Alton E W F W. Eur Resp J 1994; 7: 2050–2056). Baseline PD values in response to perfusion (4 ml per min) of Krebs' HEPES solution (pH7.4) are allowed to stabilize and are subsequently recorded for 2 min. The perfusing solution was then changed sequentially to Kreb's HEPES plus 100 µm amiloride for 4 min, low chloride Kreb's HEPES (chloride replaced by gluconate) plus 100 µm amiloride for 6 min, and finally low chloride Kreb's HEPES plus 100 µm amiloride and 10 µm isoprenaline for 5 min. All solutions are at room temperature. PD is recorded every second by a custom-built, better-powered, data logger (Logan-Sinclair, Rochester, UK) except for patients 5, 6, 7 and 8 on day 3, and patient 5 on day 5, where data were recorded manually. Measurements are taken from both nostrils on each measurement day. Values of basal PD, the change in PD after amiloride treatment (ΔPDamil), the change in PD after low chloride substitution (ΔPDCl$^-$) and the change in PD after isoprenaline treatment (ΔPDIso) are obtained by averaging the PD values for the last 60 s in each solution from both nostrils. For discussion purposes, increases and decreases in PD refer to absolute magnitude of the PD. The Mann-Whitney U test for comparison between data sets is used as in Caplen et al 1995, and the null hypothesis of no difference is rejected at P>0.05.

Study results confirm that the use of cationic liposomes to facilitate CFTR gene transfer is safe, with no adverse effects observed even at the highest dose administered, and feasible. Most of the CFTR-treated patients show evidence of CFTR function by transepithelial PD measurement or by LZQ analysis.

Cited References

Biwersi, J., and A. S. Verkman. 1991. *Biochemistry* 30:7879–7883.
Biwersi, J., et al. 1992. *Am. J. Physiol.* 262:C242–250.
Biwersi, J., B. Tulk, and A. S. Verkman. 1994. *Anal. Biochem.* 219:139–143.
Biwersi, J., and A. S. Verkman. 1994. *Am. J. Physiol.* 266:C149–156.
Brown, C. R., et al. 1996. *Cell Stress Chaperones* 1:117–125.
Burdzy, A., et al. 1998. *Nucleosides and Nucleotides*, 17:143–151.
Caplen et al *Nature Med* 1995; 1: 39–46
Chao, A. C., J. A. Dix, M. Sellers, and A. S. Verkman. 1989. *Biophys. J.* 56:1071–1081.
Cheng et al., 1991 *Cell* 66, 1027–36
Cheng et al., 1995 *Am J Physiol* 268, L615–24
Chiu, et al., Science Mar 19 1999, 283:1892–1895
Delaney et al. 1993 *Nat Genet* 4, 426–31
Dho and Foskett 1993 *Biochim Biophys Acta* 1152, 83–90.
Dupuit et al. 1997 *Hum Gene Ther* 8, 1439–50.
Fushimi, K., and A. S. Verkman. 1991. *J. Cell Biol.* 112:719–725.
Gao X, Huang L. *Biochem Biophy Res Commun.* 1991; 179: 280–285
Gill, D. R., et al. 1997. *Gene Ther.* 4:199–209.
Grubman et al. 1995 *Gastroenterology* 108, 584–592
Howard et al., 1996a *Nat Med* 2, 467–9
Howard et al., 1996b *Kidney Int* 49, 1642–8
Illsley, N. P., and A. S. Verkman. 1987. *Biochemistry* 26:1215–1219.
Jayaraman, S., and A. S. Verkman. 1999. *Biophys. J.* 76:A359.
Jayararnan, S., J. Biwersi, and A. S. Verkman. 1999. *Am J. Physiol.* 276 in press.
Jiang, C., et al. 1998. *Am. J. Physiol.* 275:C171–178.
Kao, H. P., J. Biwersi, and A. S. Verkman. 1992. *Proc. S.P.I.E.* 1648:194–201.
Ma, T., et al.1993. *J. Biol. Chem.* 268:22756–22764.
MacVinish L J, et al. Am J Physiol. 1997a Aug;273(2 Pt 1):C734–40
MacVinish L J et al. J Physiol (Lond) 1997b Mar 15; 499(Pt 3):677–87
Marshall et al. 1994 *J. Biol. Chem.* 269:2987–95.
McLachlan, G., et al. 1996. *Gene Ther.* 3:1113–1123.
Mansoura et al., Apr. 10, 1999, in *Hum Gene Ther* vol 10.
Ostedgaard et al. 1997 *Biochemistry* 36, 1287–94.
Porteous, D. J., et al. 1997. *Gene Ther.* 4:210–218.
Ram and Kirk 1989 *Proc Natl Acad Sci USA* 86, 10166–70.
Rich et al. 1990 *Nature* 347, 358–63.
Rich et al., 1993 *J. Biol. Chem.* 268:22756–22764.
Rommens et al. 1991 *Proc Natl Acad Sci USA* 88, 7500–4.
Schwiebert et al. 1994 *Am J Physiol* 267, C272–81.
Skalski, B., et al. 1987. *Tetrahedron* 43:3955–3961.
Skalski, B., et al. 1989. *J. Chem. Soc. Perkin Trans.* II 1989:1691–1696.
Skalski, B., R. P. Steer, and R. E. Verrall. 1990. *J. Am. Chem. Soc.* 113:1756–1762.
Sorgi F L, Huang L. *Neuroreport.* 1997 Jul 7;8(9–10) :2355–8)
Srinivas, S. P., and J. A. Bonanno. 1997. *Am. J. Physiol.* 272: C1404–C1414.
Stern et al. 1995 *Gene Ther* 2, 766–74.
Verkman, A. S. 1990. *Am. J. Physiol.* 259:C375–C388.
Verkman, A. S., M. Armijo, and K. Fushimi. 1991. *Biophys. Chem.* 40:117–125.
Verkman et al. 1992 *Am J. Physiol* 262, C23–31.
Verkman, A. S., and J. Biwersi. 1995 In: *Methods in Neurosciences* (J. Kraicer, and S. J. Dixon, eds.), Academic Press, pp. 328–339.
West and Molloy 1996 *Anal Biochem* 241, 51–8.
Xie et al. 1995 *J. Biol. Chem.* 270:28084–91.
Yang et al. 1993 *Hum Mol Genet* 2, 1253–61.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound comprising the general formula:

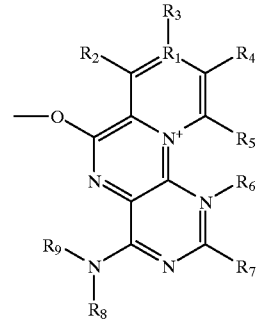

wherein $R_1$ is selected from C and N;

$R_2$–$R_9$ are independently hydrogen or substituted or unsubstituted forms of a moiety selected from the group consisting of alkyl, alkenyl, alkynyl, aryl, heteroalkyl, heteroaryl, and acyl, wherein at least one of $R_2$–$R_9$ is a substituent other than hydrogen and R6 is an optional substituent, wherein said compound has a limitation selected from the group consisting of:

(a) one or more of the pairs $R_2$ and $R_3$; $R_3$ and $R_4$; $R_4$ and $R_5$; and $R_6$ and $R_7$; and $R_8$ and $R_9$, may be directly or indirectly further covalently connected, to form a substituted or unsubstituted, aromatic or nonaromatic ring structure;

(b) one or more of $R_2$–$R_7$ comprise a functional group selected from a conjugation group, a polarity enhancing group and a iodide sensitivity enhancing group; and (c) $R_1$ is N.

2. The compound of claim 1, wherein the functional group is a conjugation group selected from —$R_{10}NR_{11}R_{12}$, —$R_{10}COOR_{13}$, and —$R_{10}X$, wherein X is halide, $R_{10}$ is alkyl and $R_{11}$–$R_{13}$ are independently selected from the group consisting of substituted or unsubstituted alkyl, alkenyl, alkynyl, aryl, heteroalkyl, heteroaryl, and acyl substituents.

3. The compound of claim 1, wherein the functional group is a polarity enhancing group selected from —$R_{10}SO_3^-$, —$R_{10}COO^-$, and —$R_{10}N^+R_{11}R_{12}R_{13}$ wherein $R_{10}$ is alkyl and $R_{11}$–$R_{13}$ are independently selected from the group consisting of substituted or unsubstituted alkyl, alkenyl, alkynyl, aryl, heteroalkyl, heteroaryl, and acyl substituents.

4. The compound of claim 1, wherein the functional group is an iodide sensitivity enhancing group selected from —$R_{10}NR_{11}R_{12}$, —$R_{10}CH_3$, —$R_{10}OCH_3$, and —$R_{10}COOR_{13}$, wherein $R_{10}$ is alkyl or a bond and $R_{11}$–$R_{13}$ are independently selected from the group consisting of substituted or unsubstituted alkyl, alkenyl, alkynyl, aryl, heteroalkyl, heteroaryl, and acyl substituents.

5. The compound of claim 1, wherein one or more of the pairs $R_2$ and $R_3$, $R_3$ and $R_4$, $R_4$ and $R_5$, $R_6$ and $R_7$, and $R_8$ and $R_9$, are directly or indirectly further covalently connected, to form a substituted or unsubstituted, aromatic or nonaromatic ring structure.

6. The compound of claim 1, wherein one or more of $R_2$–$R_5$ comprises the functional group.

7. The compound of claim 2, wherein $R_{10}$ is $(CH_2)_n$, wherein n is an integer from 0–3.

8. The compound of claim 3, wherein $R_{10}$ is $(CH_2)_n$, wherein n is an integer from 0–3.

9. The compound of claim 4, wherein $R_{10}$ is $(CH_2)_n$, wherein n is an integer from 0–3.

10. The compound of claim 1, wherein $R_1$ is N.

11. The compound of claim 1, wherein $R_1$ is C; $R_2$, $R_3$, $R_5$, $R_6$, $R_7$ and $R_9$ are H; $R_8$ is a polyhydroxylated cycloalkyl or cycloheteroalkyl; and $R_4$ comprises a functional group.

12. The compound of claim 1, wherein $R_1$ is C; $R_3$, $R_5$, $R_7$ and $R_9$ are H; $R_8$ is a polyhydroxylated cycloalkyl or cycloheteroalkyl; one of $R_2$, $R_4$ and $R_6$ comprises a functional group and the remaining two of $R_2$, $R_4$ and $R_6$ are H, wherein the functional group is a conjugation group selected from —$R_{10}NR_{11}R_{12}$, —$R_{10}COOR_{13}$, and —$R_{10}X$, wherein X is halide, $R_{10}$ is alkyl and $R_{11}$–$R_{13}$ are independently selected from the group consisting of substituted or unsubstituted alkyl, alkenyl, alkyl, aryl, heteroalkyl, heteroaryl, and acyl substituents.

13. The compound of claim 1, wherein $R_1$ is C; $R_3$, $R_5$, $R_7$ and $R_9$ are H; $R_8$ is a polyhydroxylated cycloalkyl or cycloheteroalkyl; one of $R_2$, $R_4$ and $R_6$ comprises a functional group and the remaining two of $R_2$, $R_4$ and $R_6$ are H, wherein the functional group is a polarity enhancing group selected from —$R_{10}SO_3^-$, —$R_{10}COO^-$, and —$R_{10}N^+R_{11}R_{12}R_{13}$ wherein $R_{10}$ is alkyl and $R_{11}$–$R_{13}$ are independently selected from the group consisting of substituted or unsubstituted alkyl, alkenyl, alkynyl, aryl, heteroalkyl, heteroaryl, and acyl substituents.

14. The compound of claim 1, wherein $R_1$ is C; $R_3$, $R_5$, $R_7$ and $R_9$ are H; $R_8$ is a polyhydroxylated cycloalkyl or cycloheteroalkyl; one of $R_2$, $R_4$ and $R_6$ comprises a functional group and the remaining two of $R_2$, $R_4$ and $R_6$ are H, wherein the functional group is an iodide sensitivity enhancing group selected from —$R_{10}NR_{11}R_{12}$, —$R_{10}CH_3$, —$R_{10}OCH_3$, and —$R_{10}COOR_{13}$, wherein $R_{10}$ is alkyl or a bond and $R_{11}$–$R_{13}$ are independently selected from the group consisting of substituted or unsubstituted alkyl, alkenyl, alkynyl, aryl, heteroalkyl, heteroaryl, and acyl substituents.

15. The compound of claim 1, wherein $R_1$ is C; $R_2$, $R_3$, $R_6$, $R_7$ and $R_9$ are H; $R_8$ is a polyhydroxylated cycloalkyl or cycloheteroalkyl, and the pair $R_4$ and $R_5$, is further covalently connected, to form a substituted or unsubstituted, aromatic ring structure.

16. The compound of claim 1, wherein $R_1$ is N; $R_2$–$R_7$ and $R_9$ are H; $R_8$ is a polyhydroxylated cycloalkyl or cycloheteroalkyl.

17. The compound of claim 1, wherein the functional group is a conjugation group and the conjugation group is coupled to a moiety selected from a membrane impermeable molecule, an optical sensor and a chromophore.

18. The compound of claim 1, wherein the compound has a molar extinction of >6000$M^{-1}cm^{-1}$ and a quantum yield of >0.1.

19. The compound of claim 1, wherein the compound has a molar extinction of >20,000$M^{-1}cm^{-1}$ and a quantum yield of >0.5.

20. The compound of claim 1, wherein the compound has an excitation wavelength of >400 nm and an emission wavelength of >500 nm.

21. The compound of claim 1, wherein the compound is fluorescent and demonstrates relatively specific iodide quenching, relatively low cytotoxicity, relatively low photo bleaching in cells, relatively uniform distribution in cells, relatively high chemical stability in cells, relatively low leakage out of cells and relatively rapid loading into cells.

22. The compound of claim 1, wherein the compound is selected from:

7-(β-D-ribofuranosylamino)-2-(n-carboxyalkyl) pyrido [2,1-h] pteridin-11-ium-5-olate, wherein n is an integer from 1 to 3;

7-(β-D-ribofuranosylamino)-2-(n-aminoalkyl) pyrido [2,1-h] pteridin-11-ium-5-olate, wherein n is an integer from 1 to 3;

7-(β-D-ribofuranosylamino)-2-(n-chloroalkyl) pyrido [2,1-h] pteridin-11-ium-5-olate, wherein n is an integer from 1 to 3;

7-(β-D-ribofuranosylamino)-2-carboxy pyrido [2,1-h] pteridin-11-ium-5-olate; and 7-(β-D-ribofuranosylamino)-2-sulfonato pyrido [2,1-h] pteridin-11-ium-5-olate.

23. A method for measuring an ion in a cell containing the compound of claim 1 comprising the step of measuring fluorescence of the compound in the vesicle.

24. A method for measuring an ion in a cell containing a compound comprising the general formula:

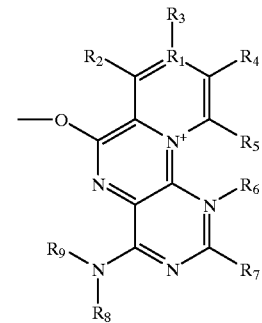

wherein $R_1$ is selected from C and N; and $R_2$–$R_9$ are independently selected from the group consisting of hydrogen and substituted or unsubstituted alkyl, alkenyl, alkynyl, aryl, heteroalkyl, heteroaryl, and acyl substituents, wherein one or more of the pairs $R_2$ and $R_3$, $R_3$ and $R_4$, $R_4$ and $R_5$, $R_6$ and $R_7$, and $R_8$ and $R_9$, may be directly or indirectly further covalently connected, to form a substituted or unstubsituted, aromatic or nonaromatic ring structure, comprising the step of measuring fluorescence of the compound in the cell.

25. The method of claim 24, wherein the compound is selected from:

4-(β-D-ribofuranosylamino)-pyrido[2,1-h]-pteridin-11-ium-5-olate (LZQ), 4-amino-pyrido[2,1-h]-pteridin-11-ium-5-olate (LMQ), 7-(β-D-ribofuranosylamino)-2-(n-carboxyalkyl) pyrido [2,1-h] pteridin-11-ium-5-olate, wherein n is an integer from 1 to 3;

7-(β-D-ribofuranosylamino)-2-(n-aminoalkyl) pyrido [2,1-h] pteridin-11-ium-5-olate, wherein n is an integer from 1 to 3;

7-(β-D-ribofuranosylamino)-2-(n-chloroalkyl) pyrido [2,1-h] pteridin-11-ium-5-olate, wherein n is an integer from 1 to 3;

7-(β-D-ribofuranosylamino)-2-carboxy pyrido [2,1-h] pteridin-11-ium-5-olate; and 7-(β-D-ribofuranosylamino)-2-sulfonato pyrido [2,1-h] pteridin-11-ium-5-olate.

26. The method of claim 24, wherein the ion is iodide.

27. The method of claim 24, wherein the cell comprises a membrane containing a functional anion transport protein or channel.

28. The method of claim 24, wherein the measuring step measures a change in fluorescence as a function of a predetermined condition.

29. The method of claim 24, wherein the cell is in vitro and the measuring step measures a change in fluorescence as a function of a predetermined condition, wherein the condition comprises the presence of a predetermined amount of a candidate modulator of ion transport in the cell.

30. The method of claim 24, wherein the cell is in situ and comprises a transgene, expression of which affects ion transport in the cell, and the measuring step measures a change in fluorescence as a function of a predetermined condition, wherein the condition comprises expression of the transgene.

* * * * *